(12) United States Patent
Schurr et al.

(10) Patent No.: US 11,034,968 B2
(45) Date of Patent: Jun. 15, 2021

(54) HETEROTROPHIC PRODUCTION METHODS FOR MICROBIAL BIOMASS AND BIOPRODUCTS

(71) Applicant: Kuehnle AgroSystems, Inc., Honolulu, HI (US)

(72) Inventors: Robert J. Schurr, Honolulu, HI (US); Adelheid R. Kuehnle, Honolulu, HI (US)

(73) Assignee: Kuehnle AgroSystems, Inc., Honolulu, HI (US)

( * ) Notice: Subject to any disclaimer, the term of this patent is extended or adjusted under 35 U.S.C. 154(b) by 88 days.

(21) Appl. No.: 15/640,246

(22) Filed: Jun. 30, 2017

(65) Prior Publication Data

US 2018/0002711 A1   Jan. 4, 2018

Related U.S. Application Data

(60) Provisional application No. 62/356,896, filed on Jun. 30, 2016.

(51) Int. Cl.

| | |
|---|---|
| *C12N 1/12* | (2006.01) |
| *C12N 15/82* | (2006.01) |
| *C12P 23/00* | (2006.01) |
| *A23K 50/80* | (2016.01) |
| *A23K 20/10* | (2016.01) |
| *A01N 65/03* | (2009.01) |
| *C12P 3/00* | (2006.01) |
| *C12P 5/02* | (2006.01) |
| *C12P 7/26* | (2006.01) |
| *C12P 9/00* | (2006.01) |
| *G01N 33/50* | (2006.01) |

(52) U.S. Cl.
CPC ............ *C12N 15/82* (2013.01); *A01N 65/03* (2013.01); *A23K 20/10* (2016.05); *A23K 50/80* (2016.05); *C12N 1/12* (2013.01); *C12P 3/00* (2013.01); *C12P 5/026* (2013.01); *C12P 7/26* (2013.01); *C12P 9/00* (2013.01); *C12P 23/00* (2013.01); *G01N 33/5097* (2013.01); *G01N 2333/405* (2013.01); *Y02E 50/30* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,882,849 A | 3/1999 | Leonard et al. |
| 6,022,701 A | 2/2000 | Boussiba et al. |
| 7,129,392 B2 | 10/2006 | Hahn |
| 7,135,620 B2 | 11/2006 | Daniell et al. |
| 7,329,789 B1 | 2/2008 | Schonemann et al. |
| 7,618,819 B2 | 11/2009 | Kuehnle |
| 8,206,721 B2 | 6/2012 | Stutz et al. |
| 8,278,090 B1 | 10/2012 | Im et al. |
| 8,404,468 B2 | 3/2013 | Lucia et al. |
| 8,911,966 B2 | 12/2014 | Martin et al. |
| 9,428,779 B2 * | 8/2016 | Yohn .................. C07K 14/405 |
| 9,487,790 B2 | 11/2016 | Champagne et al. |
| 2008/0038774 A1 * | 2/2008 | Higashiyama ......... A23D 9/007 435/67 |
| 2009/0214475 A1 | 8/2009 | Hu et al. |
| 2009/0317878 A1 | 12/2009 | Champagne et al. |
| 2010/0316720 A1 | 12/2010 | Stutz et al. |
| 2012/0171733 A1 | 7/2012 | Im et al. |
| 2012/0264195 P1 | 10/2012 | Biel et al. |
| 2015/0232802 A1 | 8/2015 | Ganuza et al. |
| 2015/0252391 A1 | 9/2015 | Li et al. |

FOREIGN PATENT DOCUMENTS

| | | |
|---|---|---|
| EP | 1501937 A2 | 2/2005 |
| EP | 1724357 A1 | 11/2006 |
| EP | 1995325 A1 | 11/2008 |
| EP | 2878676 A2 | 6/2015 |
| WO | WO-2003/027267 A1 | 4/2003 |

OTHER PUBLICATIONS

Xian-Ming Shi et al. Biotechnol Prog, 2002, 18, 723-727.*
Kobayashi et al. Journal of Fermentation and Bioengineering. 1992, vol. 74, No. 1, pp. 17-20.*
Chen et al. Process Biochemistry, 1996, vol. 31, No. 6, pp. 601-604.*
Chen et al. "High cell density culture of Chlamydomonas reinhardtii on acetate using fed batch and hollow fibre cell-recycle systems". Bioresource Technology. 1996, 55, pp. 103-110.*
Minxi Wan et al. "Sequential heterotrophy-dilution-photoinduction cultivation of Haematococcus pluvialis for efficient production of astaxanthin". Bioresource Technology. 2015, 198, pp. 557-563.*

(Continued)

*Primary Examiner* — Vera Afremova
(74) *Attorney, Agent, or Firm* — Saliwanchik, Lloyd & Eisenschenk

(57) ABSTRACT

The invention pertains to a method for synthesizing a product of interest by culturing a microalgal cell producing the product of interest in the dark in a culture medium comprising an organic acid as a fixed carbon source, wherein the microalgal cell is a facultative heterotroph. The product of interest can be a microalgal biomass, a pigment, terpene, recombinant molecule, biogas, or a precursor thereof. In an embodiment, the culture medium comprises urea as a primary source of nitrogen. In one embodiment, the microalgal cell belongs to the order Chlamydomonadales. A method of identifying and isolating a microalgal cell having a preferred characteristic that is suitable for synthesis of a product of interest is also provided, the method comprising identifying and isolating a non-mutagenized or recombinant microalgal cell from a microalgal culture using a fluorescence activated cell sorting technique and/or a phototaxic response.

40 Claims, 4 Drawing Sheets
Specification includes a Sequence Listing.

(56) References Cited

OTHER PUBLICATIONS

International Search Report and Written Opinion dated Oct. 20, 2017 issued in International Application No. PCT/US2017/040486, filed Jun. 30, 2017.
Shah, MD. Mahfuzur R. et al., Astaxanthin-Producing Green Microalga *Haematococcus pluvialis*: From Single Cell to High Value Commercial Products, Frontiers in Plant Science, Apr. 28, 2016, 7(531):1-28.
Zhang, Zhen et al., A New Paradigm for Producing Astaxanthin From the Unicellular Green Alga *Haematococcus pluvialis*, Biotechnology and Bioengineering, Oct. 2016, 113(10):2088-2099, Wiley Periodicals, Inc.
Minhas, Amritpreet K. et al., A Review on the Assessment of Stress Conditions for Simultaneous Production of Microalgal Lipids and Carotenoids, Frontiers in Microbiology, May 3, 2016, 7(546):1-19.
Figueroa-Martinez, Francisco et al., When the lights go out: the evolutionary fate of free-living colorless green algae, New Phytologist, 2015, 206(3):972-982.
Kuehnle, Adelheid et al., Some Microalgae from the Hawaiian Islands with a Focus on Industrial Applications, Current Biotechnology, 2015, 4(4):499-513, Bentham Science Publishers.
Terashima, Mia et al., A fluorescence-activated cell sorting-based strategy for rapid isolation of high-lipid *Chlamydomonas* mutants, The Plant Journal, 2015, 81(1):147-159, Society for Experimental Biology and John Wiley & Sons Ltd.
Schurr, Robert et al., Microalgae Crop Improvement: Tools for Quality Control and Molecular Breeding, Industrial Biotechnology, Jun. 2014, 10(3):237-243, Mary Ann Liebert, Inc.
Zhou, Y. et al., Characterization of a *Chlamydomonas reinhardtii* mutant strain with improved biomass production under low light and mixotrophic conditions, Algal Research, 2015, 11:134-147, Elsevier B.V.
Kumar, Anil et al., Development of an RNAi based microalgal larvicide to control mosquitoes, Malaria World Journal, Mar. 2013, 4(6):1-7.
Kobayashi, Makio et al., Light-independent, astaxanthin production by the green microalga *Haematococcus pluvialis* under salt stress, Biotechnology Letters, Jun. 1997, 19(6):507-509, Kluwer Academic Publishers.
Kobayashi, Makio et al., Growth and Astaxanthin Formation of *Haematococcus pluvialis* in Heterotrophic and Mixotrophic Conditions, Journal of Fermentation and Bioengineering, 1992, 74(1):17-20, Elsevier B.V.
Kim, Eunseong et al., A Transformed Bacterium Expressing Double-Stranded RNA Specific to Integrin β1 Enhances Bt Toxin Efficacy against a Polyphagous Insect Pest, *Spodoptera exigua*, PLoS ONE, Jul. 14, 2015, 10(7):1-15.
Kazamia, Elena et al., An Engineered Community Approach for Industrial Cultivation of Microalgae, Industrial Biotechnology, Jun. 2014, 10(3):184-190, Mary Ann Liebert, Inc.
Hatlen, B. et al., Growth performance, feed utilization and product quality in slaughter size Atlantic salmon (*Salmo salar* L.) fed a diet with porcine blood meal, poultry oil and salmon oil, Aquaculture Nutrition, 2013, 19(4):573-584, John Wiley & Sons Ltd.
Hata, Norihiko et al., Production of astaxanthin by *Haematococcus pluvialis* in a sequential heterotrophic-photoautotrophic culture, Journal of Applied Phycology, 2001, 13(5):395-402, Kluwer Academic Publishers.
Göksan, Tolga et al., Growth Characteristics of the Alga *Haematococcus pluvialis* Flotow as Affected by Nitrogen Source, Vitamin, Light and Aeration, Turkish Journal of Fisheries and Aquatic Sciences, 2011, 11:377-383, Central Fisheries Research Institute (CFRI), Trabzon, Turkey.
Gimpel, Javier A. et al., In Metabolic Engineering of Eukaryotic Microalgae: Potential and Challenges Come with Great Diversity, Frontiers in Microbiology, Dec. 15, 2015, 6:1376, doi: 10.3389/fmicb.2015.01376.
Feng, Shuying et al., *Dunaliella salina* as a novel host for the production of recombinant proteins, Applied Microbiology Biotechnology, 2014, 98(10):4293-4300, Springer-Verlag Berlin Heidelberg.
Fábregas, Jaime et al., Two-stage cultures for the production of Astaxanthin from *Haematococcus pluvialis*, Journal of Biotechnology, 2011, 89(1):65-71, Elsevier Science B.V.
Doebbe, Anja et al., Functional integration of the *HUP1* hexose symporter gene into the genome of *C. reinhardtii*: Impacts on biological H2 production, 2007, 131(1):27-33, Elsevier Science B.V.
Chua, Penelope R. et al., Production of Soladiesel from Cellulose Feedstocks, Energy Research and Development Division Final Project Report, 2011, pp. 1-36, California Energy Commision.
Chisti, Y. et al., Fermentation (Industrial): Basic Conditions, Encyclopedia of Food Microbiology, 1999, pp. 663-674, Academic Press, London.
Chen, T. et al., Construction of Dunaliella salina heterotrophic expression vectors and identification of heterotrophically transformed algal strains, Sheng Wu Gong Cheng Xue Bao (Chinese Journal of Biotechnology), Mar. 2009, 25(3):392-398, English abstract only.
Chen, Toa et al., Employment of Organic Acids to Enhance Astaxanthin Formation in Heterotrophic *Chlorella zofingiensis*, Journal of Food Processing and Preservation, Apr. 2009, 33(2):271-284, Wiley Periodicals, Inc,.
Chekanov, Konstantin et al., Accumulation of Astaxanthin by a New *Haematococcus pluvialis* Strain BM1 from the White Sea Coastal Rocks (Russia), Marine Drugs, Aug. 15, 2014, 12(8):4504-4520.
Cerutti, Heriberto et al., RNA-Mediated Silencing in Algae: Biological Roles and Tools for Analysis of Gene Function, Eukaryotic Cell, Sep. 2011, 10(9):1164-1172, American Society for Microbiology.
Bumbak, Fabian et al., Best practices in heterotrophic high-cell-density microalgal processes: achievements, potential and possible limitations, Applied Microbiology and Biotechnology, 2011, 91(1):31-46, Springer Science & Business Media B.V.
Boyle, Nanette R. et al., Flux balance analysis of primary metabolism in *Chlamydomonas reinhardtii*, BMC Systems Biology, Jan. 7, 2009, 3:4, doi: 10.1186/1752-0509-3-4.
Ben-Amotz, Ami et al., Massive Accumulation of Phytoene Induced by Norflurazon in *Dunaliella bardawil* (Chlorophyceae) Prevents Recovery From Photoinhibition, Journal of Phycology, 1987, 23(1):176-181.
Barbosa, M.J. et al., Effect of carotenoid source and dietary lipid content on blood astaxanthin concentration in rainbow trout (*Oncorhynchus mykiss*), Aquaculture, 1999, 176(3-4):331-341, Elsevier Science B.V.
Bar, Etan et al., Pigment and Structural Changes in *Chlorella zofingiensis* upon Light and Nitrogen Stress, Journal of Plant Physiology, 1995, 146(4):527-534, Elsevier GmbH.
Ambati, Ranga Rao et al., Astaxanthin: Sources, Extraction, Stability, Biological Activities and Its Commercial Application—A Review, Marine Drugs, Jan. 2014, 12(1):128-152, Multidisciplinary Digital Publishing Institute (MDPI), Basel, Switzerland.
Alonso-Gutierrez, Jorge et al., Metabolic engineering of *Escherichia coli* for limonene and perillyl alcohol production, Metabolic Engineering, 2013, 19:33-41, Elsevier Inc.
Alabi, Abayomi O. et al., Microalgae technologies & processes for biofuels/bioenergy production in British Columbia: Current Technology, Suitability, & Barriers to Implementation: Final Report, Jan. 14, 2009, pp. 1-88, The British Columbia Innovation Council.
Aflalo, Claude et al., On the Relative Efficiency of Two- vs. One-stage Production of Astaxanthin by the Green Alga *Haematococcus pluvialis*, Biotechnology and Bioengineering, Sep. 1, 2007, 98(1):300-305, Wiley Periodicals, Inc.
Rise, Moshe et al., Accumulation of Secondary Carotenoids in *Chlorella zofingiensis*, Journal of Plant Physiology, 1994, 144(3):287-292, Elsevier GmbH.
Orosa, M. et al., Production and analysis of secondary carotenoids in green algae, Journal of Applied Phycology, Oct. 2000, 12(3):553-556, Kluwer Academic Publishers.
Muhaemin, Moh. et al., Biomass Nutrient Profiles of Marine Microalgae *Dunaliella safina*, Jurnal Penelitian Sains, Sep. 2010, 13(3(D)):13313-64-13313-67, FMIPA Universitas Sriwijaya.

(56) References Cited

OTHER PUBLICATIONS

Morales-Sánchez, Daniela et al., Heterotrophic growth of microalgae: metabolic aspects, World Journal of Microbiology and Biotechnology, 2015, 31(1):1-9, Springer Netherlands.

McVittie, Anne et al., Flagellum Mutants of *Chlamydomonas reinhardii*, Journal of General Microbiology, Mar. 1, 1972, 71(3):525-540, Great Britain.

McCarthy, Sarah S. et al., White Mutants of *Chlamydomonas reinhardtii* are Defective in Phytoene Synthase, Genetics, Nov. 2004, 168(3):1249-1257, Genetics Society of America.

Machado, Vilmar et al., RNA Interference: A new Strategy in the Evolutionary Arms Race Between Human Control Strategies and Insect Pests, Folia Biologica (Krakow), 2014, 62(4):335-343, Institute of Systematics and Evolution of Animal, PAS.

Lorenz, R. Todd et al., Commercial potential for *Haematococcus* microalgae as a natural source of astaxanthin, Trends in Biotechnology, Apr. 2000, 18:160-167, Elsevier Science Ltd.

Lorenz, R.Todd, A Technical Review of *Haematococcus* Algae, Cyanotech Corporation: Technical Bulletin #060, 1999.

Liu, Xuebo et al., Cis astaxanthin and especially 9-cis astaxanthin exhibits a higher antioxidant activity in vitro compared to the all-trans isomer, Biochemical and Biophysical Research Communications, 2007, 357(1):187-193, Elsevier Inc.

Lewis, Louise A. et al., Green algae and the origin of land plants, American Journal of Botany, 2004, 91(10):1535-1556.

Lee, Yuan-Kun et al., Production of astaxanthin by *Haematococcus*, Chemicals from Microalgae, 1999, pp. 173-195.

Lauersen, Kyle J. et al., Efficient recombinant protein production and secretion from nuclear transgenes in *Chlamydomonas reinhardtii*, Journal of Biotechnology, 2013, 167(2):101-110, Elsevier B.V.

Zhang, Jiang et al., Full crop protection from an insect pest by expression of long double-stranded RNAs in plastids, Science, Feb. 27, 2015, 347(6225):991-994, American Association for the Advancement of Science, Washington, D.C., United States of America.

Zhang, Xue-Wu et al., Kinetic models for heterotrophic growth of *Chlamydomonas reinhardtii* in batch and fed-batch cultures, Process Biochemistry, 1999, 35(3-4):385-389, Elsevier Science Ltd.

Yuan, Jian-Ping et al., Potential health-promoting effects of astaxanthin: A high-value carotenoid mostly from microalgae, Molecular Nutrition & Food Research, 2011, 55(1):150-165, Wiley-VCH Verlag GmbH & Co. KGaA, Weinheim.

Yu, J. et al., Biophotolysis-based Hydrogen Production by Cyanobacteria and Green Microalgae, Communicating Current Research and Educational Topics and Trends in Applied Microbiology, 2007, pp. 79-89, Formatex.

Wrolstad, Ronald E. et al., Alternatives to Those Artificial FD&C Food Colorants, Annual Review of Food Science and Technology, 2012, 3:59-77, Annual Reviews.

Wang, Xin et al., Photosynthetic terpene hydrocarbon production for fuels and chemicals, Plant Biotechnology Journal, 2015, 13(2):137-146, Society for Experimental Biology, Association of Applied Biologists and John Wily & Sons Ltd.

Wang, Y. et al., Growth-associated biosynthesis of astaxanthin in heterotrophic *Chlorella zofingiensis* (Chlorophyta), World Journal of Microbial Biotechnology, 2008, 24(9):1915-1922, Springer Netherlands.

Ukibe, Ken et al., Efficient screening for astaxanthin-overproducing mutants of the yeast *Xanthophyllomyces dendrorhous* by flow cytometry, FEMS Microbiology Letters, 2008, 286(2):241248, Blackwell Publishing Ltd.

Tran, Duc et al., Identification of Dunaliella Viridis Using its Markers, International Journal of Applied Science and Technology, Apr. 2013, 3(4):118-126, Center for Promoting Ideas, USA.

Tjahjono, Agus Eko et al., Hyper-accumulation of astaxanthin in a green alga *Haematococcus pluvialis* at elevated temperatures, Biotechnology Letters, Feb. 1994, 16(2):133-138, Kluwer Academic Publishers.

Syrenne, Ryan D. et al., Production of Limonene, a Volatile Monoterpene, in the Freshwater Algae *Chlamydomonas reinhardtii*, Algal Biology, 2014, pp. 27-28, National Alliance for Advanced Biofuels and Bioproducts Synopsis (NAABB).

Stemmer, Willem P.C. etal., Single-step assembly of a gene and entire plasmid from large numbers of oligodeoxyribonucleotides, Gene, 1995, 164(1):49-53, Elsevier Science B.V.

Spijkerman, Elly et al., Elemental and fatty acid composition of snow algae in Arctic habitats, Frontiers in Microbiology, Oct. 29, 2012, 3(380):1-15.

Somchai, Parinyachat et al., Use of microalgae *Chlamydomonas reinhardtii* for production of double-stranded RNA against shrimp virus, Aquaculture Reports, May 2016, 3:178-183, Elsevier B.V.

Solymosi, K. et al., Food colour additives of natural origin, Colour Additives for Foods and Beverages, Mar. 2015, p. 3-34, Woodhead Publishing.

Sharon-Gojman, Revital et al., Advanced methods for genetic engineering of *Haematococcus pluvialis* (Chlorophyceae, Volvocales), Algal Research, 2015, 10:8-15, Elsevier B.V.

Scranton, Melissa A. et al., *Chlamydomonas* as a model for biofuels and bio-products production, The Plant Journal, 2015, 82(3):523-531.

Schmidt, Isabell et al., Biotechnological production of astaxanthin with *Phaffia rhodozyma/Xanthophyllomyces dendrorhous*, Applied Microbiology and Biotechnology, 2011, 89(3):555-571, Springer-Verlag.

Scaife, Mark A. et al., Establishing *Chlamydomonas reinhardtii* as an industrial biotechnology host, The Plant Journal, 2015, 82(3):532-546.

Sambrook, Joseph et al., Protocol 6: Cloning PCR Products by Addition of Restriction Sites to the Termini of Amplified DNA, Molecular Cloning: A Laboratory Manual, Third Edition, Jan. 15, 2001, 2(8):37-41, Cold Spring Harbor Laboratory Press, New York.

Office Action dated Mar. 16, 2021 in European Application No. 17740210.4.

\* cited by examiner

HETEROTROPHIC PRODUCTION METHODS FOR MICROBIAL BIOMASS AND BIOPRODUCTS

FIELD OF THE INVENTION

The present invention pertains to improved fermentation methods for producing biomass and bioproducts from microorganisms. In one embodiment, the present invention relates to fermentation methods employing heterotrophically culturing facultative heterotrophic microorganisms for extended accelerated growth, for example, to higher cell densities, and production of useful compounds without the requirement of photoinduction and cellular differentiation. The microorganisms of the invention can be selected, mutated, or genetically engineered for use in the methods or other aspects of the invention described herein.

BACKGROUND OF THE INVENTION

There is a growing global consumer demand for affordable natural, safe, and efficacious products affecting their long-term health while protecting the environment. Recombinant molecules expressed in microorganisms can replace unsustainable or problematic products or ingredients currently used in the marketplace. Isoprenoids constitute another large class of compounds that comprise ingredients in such products. Recombinant technology and the isoprenoid pathway generate numerous commercially useful target compounds, with non-limiting examples such as pigments, terpenes, rubber, vitamins, fragrances, flavorings, solvents, steroids/sterols, hormones/growth regulators, feed additives, nutritional compounds, lubricant additives, and even insecticides. These in turn are used in products for food and beverages, perfumes, feed, cosmetics, and raw materials for chemicals, nutraceuticals, pharmaceuticals and other industrial applications.

One such isoprenoid is a class of natural pigmented compounds called carotenoids, used as antioxidants, anti-inflammatories and colorants. Humans rely on carotenoids as their primary source of antioxidants. The orange-red pigment astaxanthin (3,3'-dihydroxy-b, b'-carotene-4,4'-dione) is considered the most potent carotenoid in existence with numerous therapeutic applications. The global market across applications for astaxanthin is projected at 670 metric tons by 2020, up from 280 metric tons in 2014. Insufficient availability and high cost of natural astaxanthin results in about 97% of the astaxanthin on the market being synthetic (designated E161J). Chemically synthesized astaxanthin is unesterified, and thus is extremely sensitive to oxidation, while its esterified form, as found in nature in microalgae, is stable and displays higher bioavailability and potency. Synthetic astaxanthin is used extensively in fish and animal feed, and to some extent in human nutritional supplements, medicinal applications, cosmetics, and skin care. As a feed additive it is used to elicit pink flesh and promote growth of farmed salmonid fish (salmon and trout), red sea bream as well as other animals. It sells at about one-third to one-sixth the price of natural algal astaxanthin. However, the practice of using synthetic chemicals derived from petroleum for colorizing food is being challenged. For this reason the US Food and Drug Administration requires retailers to label farmed salmon and trout as 'color added'.

In order to displace the use of synthetic pigments, a much lower cost natural counterpart is needed. Aerobic fermentation of *Phaffia rhodozyma* (*Xanthophyllomyces dendrorhous*) yeast—a eukaryotic microorganism like microalgae—yields a non-esterified free astaxanthin as a 3R, 3'R isomer in chemical form that is non-identical and inferior to the prevalent and preferred form found in microalgae and in wild salmon. For the latter, usually more than 95% of total astaxanthin is in the form of monoester and diesters as a 3S, 3'S isomer. The *Phaffia* astaxanthin selling price is much lower than that of microalgal astaxanthin but still higher than that synthesized chemically. Disadvantageously, while *Phaffia* has a fast growth rate it has relatively low pigment content, resulting in unsustainable high production costs for low yields.

Fermentative production targets for astaxanthin from *Phaffia* have recently been modeled to be cost competitive with synthetic astaxanthin if certain metrics are met as follows: Productivity of 2 mg/L-hour carotenoids; harvest density of 60 g/L; and astaxanthin yield of 4 mg/g (0.4%) dry weight, all within a cycle time of 120 hours. Using this framework as one example, productivity metrics can be proportionally adjusted to set competitive metrics for fermentor-based heterotrophic production of astaxanthin from other microorganisms such as microalgae; and further adjusted for production of carotenoid precursors and related isoprenoid molecules of differing values. Economic and sustainability calculations can also be made factoring in the use of organic acids rather than glucose used for *Phaffia*.

A problem is that to date all industrial production of astaxanthin from microalgae employs photosynthesis performed either outdoors or indoors and in sunlight or under artificial illumination by methods that cultivate the algae in submerged cultures in raceway/ponds and photobioreactors and from only one type of microalgae, *Haematococcus* of the Chlamydomonadales. The most common industrial species is *Haematococcus pluvialis*. This algae is the richest source of the carotenoids, usually producing up to 3%, or even 5%, astaxanthin of its dry weight as cysts (Lorenz and Cysewski 2000; U.S. Pat. No. 6,022,701). Other carotenoids such as beta-carotene, canthaxanthin and lutein are also present, originating from acetyl-CoA through isopentenyl pyrophosphate (IPP) and phytoene to the pigmented precursors and finally astaxanthin. Together they provide a useful and healthful cocktail of molecules not provided in synthetic astaxanthin.

Another problem is that the current production of astaxanthin from *Haematococcus* is fraught with challenges that limit supply. The shortage of natural pigment drives the high pricing. As a result, while synthetic astaxanthin is largely relegated to use as colorants in the high volume aquaculture and animal feed sector, microalgal astaxanthin is the main source for human applications such as dietary supplements and cosmetics. Disadvantageously, even if natural algal astaxanthin were to be price competitive with synthetic, meeting feed volumes of about 300 tons pigment would require 10,000 tons algal biomass produced for extraction (assuming 3% pigment content), over ten times what is produced today photosynthetically.

One of the astaxanthin production challenges involves the complex life cycle of *Haematococcus*, requiring cellular differentiation from green vegetative macrozooids to red aplanospores (haematocysts). The basal astaxanthin content in the vegetative stage of about 10 pg/cell increases during the encystment process with the formation of brown-red, non-flagellated, non-motile immature cysts with about 30 pg/cell and then mature cysts with about 613 pg/cell. The process suffers from the long period of time required for induction of encystment and accumulation of astaxanthin, which alone exceeds the typical 7-10 days (168-240 hours)

total cycle time used for batch and fed-batch industrial fermentation of submerged cultures, including for *Phaffia* yeast.

Patent application WO2003027267 teaches a light-dependent process for producing a biomass enriched with astaxanthin by cultivating *Haematococcus pluvialis* through two stages: Stage 1, a green motile, biflagellate stage during which the cells are capable of photosynthetic autotrophic growth; and Stage 2, an encystment stage during which, under unfavorable conditions, these cells form cysts by losing their motility, accompanied by the synthesis of astaxanthin and other carotenoids in large quantities. The unfavorable conditions consist of one or more of intense light, depletion of nutrients, or changes in temperature, pH or salinity, which cause the organism to form cysts as a protective response. While the process described in WO2003027267 uses an open pond system, U.S. Pat. Nos. 6,022,701 and 5,882,849 teach similar light-dependent two-stage processes enabled by use of photobioreactors in various configurations and combinations of photobioreactors and ponds. U.S. Pat. No. 6,022,701 further teaches use of nutrient-replete medium for vegetative growth under light followed by use of nutrient-deplete medium to induce accumulation of astaxanthin under light in the presence of inorganic carbon (carbon dioxide).

Such processes are disadvantaged by being dependent on light for photosynthesis to grow biomass, and by being dependent on the two-stage process of culturing to transform green motile cells into red cysts prior to harvesting the astaxanthin-rich biomass therefrom. Light is commonly supplied by sunlight, and thus inclement weather, seasonality or growing degree days, pollution that diminishes light, and geographic location make for variable productivity and also diminished productivity. Culture crashes or loss in biomass due to predation by protozoa also leads to further diminished productivity. In the case of indoor raceways or photobioreactors, sunlight can be replaced by artificial illumination, but it still requires sufficient surface area and appropriate culture handling for exposure to light, and it still requires a green and red phase for astaxanthin production. The two-stage culture methods involve complex culture manipulations and require many days until harvest, usually 7-10 days for the encystment stage alone, thus adding significant time beyond the biomass growth phase for completion of a full production and harvest cycle. These cysts are indigestible with thick rigid cell walls and must be broken open or comminuted to access the pigments for extraction, product formulation, or bioavailability.

Examples of the two-step production method are not unique to *Haematococcus*. For example, culturing of various types of algae such as from the related taxa *Chlamydomonas, Chloromonas*, and *Chlamydocapsa* described in U.S. Pat. No. 8,206,721, proceeds with a two-stage culturing process in order to first generate biomass under light followed by harvesting done in the second or red stage of cells differentiated into cysts or spores.

Advantageously, several microalgae have been shown to be facultative heterotrophs for cultivation in the dark whereby carbon dioxide used during photosynthesis as the carbon growth source is substituted by some other carbon source dissolved in the nutrient medium. Aerobic fermentation of heterotrophic algae is performed using generally similar fermentor tanks and operations as seen for other microorganisms in industrial fermentation facilities. In general, the use of fermentation processes can be significantly advantaged over photosynthetic (phototrophic) production due to much higher productivities, a reduced footprint so as not to compete with other land uses, management of contamination, management of containment of recombinant organisms, lower water use to meet large volume production, and year-round production in any climates. Indeed, fermentation is considered the most economical and scalable method of algae production.

Nevertheless, methods to produce algae heterotrophically are not routine, such that several microalgae may demonstrate heterotrophy at small lab scale but the majority requires development in order to transition into economic manufacturing. Among the green algae, some members of the Chlorellales have been successfully transitioned to industrial scale manufacturing employing dark fermentation. These are cultivated using hexoses and pentoses as their fixed carbon source in dark heterotrophic culture. One example is *Chlorella*. Organic acids, if supplied at some point in addition to the sugars in the medium that provide the primary fixed carbon source, would serve to induce the formation of pigments. For example, in *Chlorella zofingiensis*, addition of pyruvate, citrate and malic acid at a concentration above 10 mM into the glucose-based culture medium stimulated biosynthesis of astaxanthin and other secondary carotenoids. In contrast, members of the Chlamydomonadales generally cannot utilize hexoses and pentoses as their primary fixed carbon source and industrial scale manufacturing solely by fermentation is not yet achieved.

The Chlamydomonadales, unlike the above mentioned Chlorellales, are sensitive to environmental and physical conditions such that the vegetative growth phase can be rapidly curtailed and encystment ensues, stymieing industrial manufacturing. There are numerous additional obstacles to heterotrophic culture of this group of microalgae.

US patent application publication no. 20080038774 teaches two-stage cultivation under dark heterotrophic conditions for *Haematococcus pluvialis*. Vegetative growth is in a medium supplemented with sodium acetate and soya bean powder or peptone, grown at a culture temperature of 16° or 20° C. for five or for six days in stationary (non-agitated) culture in flasks of 100 mL culture, followed by an encystment period with astaxanthin production induced using introduced elevated sodium acetate for high salinity and high culture temperature of 30° C. for a further 8 days to reach up to 80 pg/cell. Disadvantageously, the process for astaxanthin production requires cellular differentiation with two morphological stages, with the astaxanthin accumulation phase being very long, similar to phototrophic ponds or photobioreactors, and the astaxanthin content achieved being only a very small fraction of that normally seen in photoinduced cysts. Disadvantageously, this process is a non-agitated process that does not scale into fermenters.

US patent application publication no. 20150252391 teaches two-stage cultivation for *Haematococcus pluvialis*, the first stage being vegetative cell growth using dark heterotrophic conditions in a medium supplemented with sodium acetate and sodium nitrate, calcium nitrate, potassium nitrate, with optional plant growth regulators, with neglible biomass growth during the first 128 or even 168 hours (5-7 days); followed by triggering cysts and astaxanthin accumulation using photoinduction with illumination of diluted cultures with associated nutrient depletion during a 5- to 7-day encystment period. Disadvantageously, this process for astaxanthin production requires cellular differentiation for two morphological stages; and the combination of phases is very long, requiring 400 hours (16.7 days) plus at least 72 hours (3 days) to produce biomass with 2.25% astaxanthin content. Disadvantageously, the process requires light, such that the culture must be transferred from the growth vessel into a photo-induction device for photo-induction of the microalgal cells. Further disadvantageously, the long cycle time includes a lag phase of 5 to 7 days.

Similarly, several combinations of light and dark stages are taught in US patent application publication no. 20150232802, with nitrogen limitation or nutrient depletion conditions effecting encystment for pigment accumulation when in the dark. Disadvantageously the process requires use of two trophic phases (light and dark), reliance on photosynthesis or use of light in one of those phases; reliance on encystment; inhibition of sustained growth on sodium acetate; use of separate physical equipment or facility for the trophic phases as well as for separation of vegetative growth phase and encystment phase, and restriction of further growth due use of N limitation for encystment.

Other obstacles to heterotrophic culture of *Haematococcus* are the low specific growth rates of 0.21/day to 0.24/day with a very long lag phase. Further, the reddening of heterotrophic biomass requires cellular differentiation in a two-stage process consisting of cell growth in darkness followed by encystment and carotenogenesis with high salt stress in darkness; or encystment and carotenogenesis after an 8-day photoinduction at elevated temperatures of 28-30° C. up from 22-25° C., producing astaxanthin content of 1.85%. A further obstacle is a requirement for elevated rates of mixing and oxygenation as is known in the art to support higher density cultures in heterotrophic fermentation. High susceptibility to hydrodynamic shearing resulting in flagellar loss and cell destruction for members of the Chlamydomonadales is problematic for achieving high cell concentration employing a non-flask bioreactor, i.e., a fermentor. A very low agitation rate in heterotrophic conditions for biomass accumulation was reported at 40 rpm, and reached a 100 rpm or less than 200 rpm only after the heterotrophic stage concluded, photoinduction occurred and cells were differentiated into the less fragile cysts, as described in EP2878676 (US patent application publication no. 20150252391). Disadvantageously, low biomass growth renders this impractical for industrial application.

Inhibition of sustained growth on sodium acetate was also problematic for a different Chlamydomonadales, *Chlamydomonas reinhardtii*, when cultured heterotrophically with sodium acetate as the fixed carbon. Although there was a reasonably high specific growth rate of 1.7/day observed, the dilution culture and near complete inhibition of growth after 40 hours is a major impediment to accumulating large amounts of biomass and bioproducts in a commercial fermentation cycle of one week and at desirable higher culture densities. This work was conducted at a low starting and final density (0.05 g/L and 1 g/L, respectively) and required addition of fresh medium as a diluent to the culture. At higher commercially relevant cell densities the requirement for sodium acetate per culture volume increases dramatically to supply enough carbon to support the mass generation, as is known in the art, resulting in inhibitory salinity levels and even earlier cessation of vegetative growth.

In these previous cases, the carbon source metabolized by heterotrophic *Haematococcus* or *Chlamydomonas* is sodium acetate, rather than the more common heterotrophic microalgal fixed carbon source of glucose. It is supplied in combination with nitrates, commonly sodium nitrate, which among numerous nitrogen sources recently tested including urea provided the best growth of photosynthetic *Haematococcus pluvialis*. The inability of some freshwater species to proliferate at elevated sodium and other salt levels that build up in the culture broth prevents sufficient biomass production required for practical mass cultivation, and in the case of *Haematococcus* and other Chlamydomonadales will trigger encystment with cessation of cell proliferation and lower resulting biomass as noted above. Disadvantageously a discontinuation of adequate levels of sodium nitrate to reduce salt will trigger spore formation with the nutrient-depleted broth.

Nutrient limitation, specifically nitrogen depletion, is a common and effective means to induce pigment accumulation above a baseline that is present in green vegetative growing cells of Chlorophytes. US patent application publication no. 20120264195 teaches that one major obstacle to use of nitrogen deprivation for the Chlamydomonadales is that vegetative growth will stop and spores and cysts will form, such as aplanospores and zygospores, with their rigid outer walls to protect it from harsh environmental conditions. Disadvantageously, a premature cessation of growth through nitrogen depletion limits productivity of culture systems with certain desired minimal production cycle times.

Taken together, the obstacles of long lag phase, slow growth rate, sensitivity to factors that prevent vegetative growth and trigger premature encystment, the long encystment period for astaxanthin accumulation, and formation of cysts themselves effectively negate any benefits of *Haematococcus* cells having elevated astaxanthin content relative to *Phaffia* for utility in typical industrial production cycles using heterotrophy. Compounding those obstacles is that the heterotrophic production methods produce low astaxanthin yield in heterotrophic biomass in the absence of light compared to that possible by phototrophic production or photoinduction. Further compounding these problems is that cysts, compared to non-rigid cells that remain motile, are more difficult to extract or digest as part of a diet, as is known in the art.

Logically, from a commercial standpoint, the microbial cell types used in heterotrophic mass cultivation should have the maximum specific growth rate and the highest, or preferred, compositional content per unit time and culture volume under optimized conditions. No cell or cell line improvement of Chlamydomonadales microalgae, including *Haematococcus* and *Chlamydomonas*, has been directed towards accumulation of sufficient biomass and target compound to benefit heterotrophic production over minimal time suited to a compact fermentation cycle, such as within a 120-hour production cycle. Cell lines selected for heterotrophic production will have benefits to economically increase productivity and lower costs. In particular, improvement of cell lines with modified levels of target compounds is desirable for optimizing efficient industrial heterotrophic fermentation that is independent of weather, climates, seasons, and geography. Target compounds of value include, but are not limited to, terpenes, carotenoids and their isoprenoid precursors and precursor derivatives.

Traditional methods for cell line improvement that involve mutagenesis and selection of individual colonies on agar plates are well known in the art. EP 1995325 describes use of carotenoid biosynthesis inhibitors norflurazon, diphenylamine and nicotine, or a mixture thereof with mutagenized photoautotrophic algae of the chlorophyceae class. U.S. Pat. No. 8,404,468 describes use of norflurazon and *Haematococcus pluvialis*, and U.S. Pat. No. 8,911,966 describes use of nicotine selection with *H. pluvialis*. Using mutagenized populations is disadvantageous because mutagenesis is random and can have other unintended or adverse consequences in the organism in aspects other than pigment accumulation. Such other aspects include, but are not limited to, growth rate, asexual reproduction, and temperature sensitivity.

Another method, flow cytometry (FCM) or fluorescence activated cell sorting (FACS), used interchangeably, was shown useful for cell line selection of astaxanthin-overproducing mutants with the carotenogenic yeast, *Phaffia*, a non-chlorophyllic organism, but unsuccessfully applied to *Haematococcus pluvialis* due to interfering autofluorescence from chlorophyll.

Yet other methods of cell line improvement employ genetic engineering. This is relevant for the methods involving Chlamydomonadales, with numerous examples including recombinant *Chlamydomonas, Haematococcus*, and *Dunaliella*.

This can include, for example, the cultivation of recombinant cells transformed with the introduction of carbon transporters. Insertion of a hexose HUP1 transporter into *Chlamydomonas reinhardtii* strain Stm6Glc4 effectively coupled an exogenous glucose supply to an enhanced biohydrogen production process. This strain still demonstrated limited heterotrophic cell growth in the dark indicating that glucose cannot replace acetate as a carbon source in *C. reinhardtii*.

The combination of this phenotype with the improved method for heterotrophic growth on organic acids provided by this invention can be powerful for improved specific productivity.

BRIEF SUMMARY OF THE INVENTION

A method for synthesizing a product of interest is provided. The method comprises the steps of:
  providing a culture medium comprising an organic acid as a fixed carbon source;
  providing a microalgal cell producing the product of interest, wherein the microalgal cell is a facultative heterotroph;
  culturing the microalgal cell in the culture medium in the dark to produce a microalgal culture from the microalgal cell;
  isolating the microalgal cells from the microalgal culture before the cells in the microalgal culture undergo cell differentiation; and
  purifying the product of interest from the microalgal culture.

The product of interest can be, but is not limited to, a microalgal biomass, a pigment, terpene, recombinant molecule, biogas, or a precursor thereof.

The method of culturing a facultative heterotroph in heterotrophic conditions as described herein provides both the active growth of biomass and the synthesis of a product of interest at a higher rate. In one embodiment, the microalgal biomass accumulates by cell division at a specific growth rate of more than 0.24/day, and is sustained over the first 96 hours and longer of culturing. In one embodiment, the product of interest is a pigment and can be produced at a specific productivity rate of more than 0.063 mg/L-hour.

The step of culturing can be conducted for a period of less than one week and without the microalgal cells undergoing cell differentiation. In certain embodiments, the microalgal cell belongs to the order Chlamydomonadales, for example, the microalgal cell can be, but is not limited to, *Haematococcus* spp., *Chlamydomonas* spp., *Chloromonas* spp., *Dunaliella* spp., or *Chlamydocapsa* spp.

In one embodiment, the microalgal cell is co-cultivated with a second cell that uses a different fixed carbon source to support its growth compared to the organic acid that supports the growth of the microalgal cell.

In another embodiment, the microalgal cell is co-cultivated with a second cell that uses the same organic acid fixed carbon source to support its growth.

In a further embodiment, the microalgal cell is achlorophyllic, non-photosynthetic, or non-flagellated.

An further embodiment provides a method of identifying and isolating a microalgal cell that is suitable for synthesis of a product of interest. The method comprises the steps of:
  culturing a microalgal strain under at least partially heterotrophic conditions to produce microalgal cells,
  identifying a non-mutagenized microalgal cell having a preferred characteristic, when grown in heterotrophic conditions, relative to the microalgal strain from which the microalgal cells are produced, where the step of identifying is performed using a fluorescence activated cell sorting technique and/or a phototaxic response; and
  isolating the non-mutagenized microalgal cell having the preferred characteristic.

In one embodiment, the step of culturing is performed under mixotrophic conditions at least for a portion of the culturing step. The preferred characteristic includes, but is not limited to, an increased synthesis of a product of interest by the microalgal cell or the absence of flagella in the microalgal cell.

BRIEF DESCRIPTION OF SEQUENCES

Figure 1:
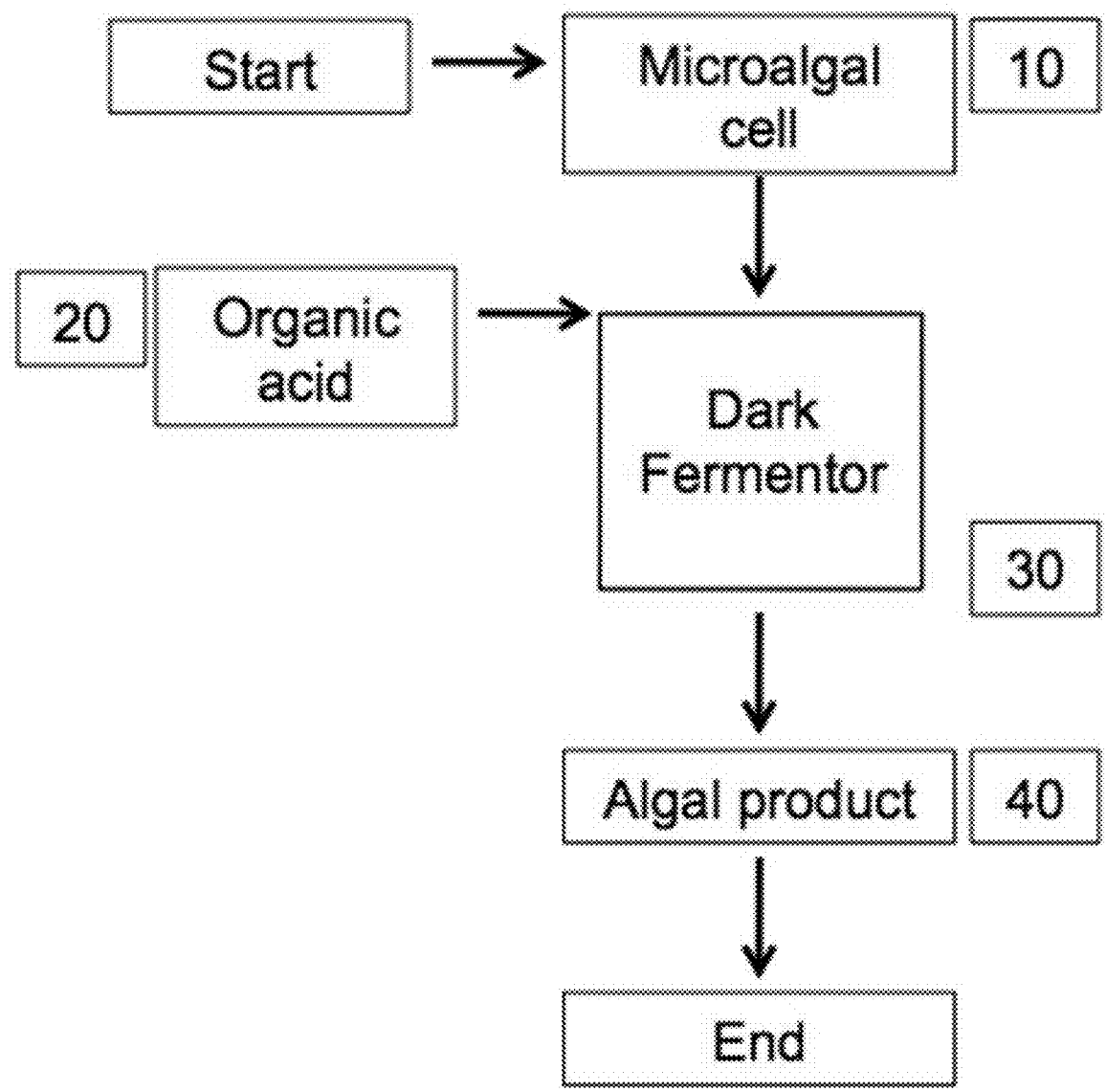
FIG. 1. A flow diagram outlining the overall method for improved heterotrophic production for microbial products. Key components in the process are highlighted. A microalgal cell (10) along with organic acid as a fixed carbon source (20) is provided in culture medium in a fermentor (30) for dark heterotrophic growth, wherein product formation is obtained in the fermentor (30) independent of exposure to light or transfer to a second vessel, and independent of cell differentiation, resulting in the output of an algal product (40). The output can be further processed as desired.

SEQ ID NO:1 shows the sequence of a primer used in the context of the instant invention.

SEQ ID NO:2 shows the sequence of a primer used in the context of the instant invention.

DETAILED DESCRIPTION OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. When ranges are used herein, combinations and subcombinations of ranges (e.g., subranges within the disclosed range), specific embodiments therein are intended to be explicitly included.

The term "photoautotrophs" refers to an organism capable of synthesizing its own food from inorganic substances using light as an energy source. Examples of photoautotrophs include green plants and photosynthetic bacteria.

The term "facultative" refers to an organism that is capable of but not restricted to a particular mode of life. For example, a facultative anaerobe can synthesize ATP by aerobic respiration if oxygen is present, but is capable of fermentation or anaerobic respiration if oxygen is absent.

The term "facultative heterotroph" refers to a photoautotrophic organism that is also capable of utilizing organic compounds for growth and/or maintenance and/or survival when light energy is not sufficient or is absent. The term also encompasses facultative heterotrophs and descendants thereof that lose their capability to perform photosynthesis, or acquire defects that result in their inability to grow as phototrophs, or are enabled to grow in the dark through genetically engineering, including for trophic conversion or for utilization of the preferred carbon feedstock.

Some representative facultative heterotrophs that can grow in the dark in the presence of acetate as a carbon source are *C. reinhardtii* and *C. dysosmos*. *Chlamydomonas* may include, but not limited to, species and strains of the *Chlamydomonas* Resource Center (see, http://www.chlamycollection.org/) and those listed in Algaebase.

*Chlamydomonas nivalis* is a collective name for red/orange pigmented *Chlamydomonas* and *Chloromonas*. The term "*Chloromonas*" refers to a related taxon also in the Chlamydomonadales order and Chlamydomonadaceae family. Various species available in culture collections are *Chloromonas rosae* UTEX SNO4, *Chloromonas brevispina* UTEX B SNO103, and *Chloromonas tughillensis* UTEX SNO92.

The term "*Chlamydocapsa*", refers to a related taxon also in the Chlamydomonadales order and Palmellopsidaceae family. Various species available in culture collections are *Chlamydocapsa* sp. CCCryo 101-99, IBMT strain collection; *C. ampla* (UTEX 291, as *Gloeocystis gigas*); *C. maxima* (UTEX 166); and *C. lobata* (CCAP 9/1).

The term "*Dunaliella*" refers to yet another related taxon in the Chlamydomonadales, in the Dunaliellaceae family (Tran et al. 2013) available in numerous recognized collections.

The term "axenic" refers to the state of a culture in which only a single species, variety, or strain of an organism is present and wherein the culture is free of all other organisms.

The term "biomass" as used herein refers to a mass of living or non-living biological material and its derivatives and includes both natural and processed, as well as natural organic materials more broadly. Thus, "microalgal biomass" and "algal biomass" refer to material produced by growth and/or propagation of microalgal cells.

"Biomass production" or "biomass accumulation" means an increase in the total number or weight of the cells of the organisms that are present in a culture over time. Biomass is typically comprised of cells; intracellular contents as well as extracellular material such as may be secreted or evolved by a cell; and can also be processed such that a fraction of the biomass is removed leaving residual biomass.

Biomass accumulation in the vegetative cell stage prior to cell differentiation into cysts is distinct from biomass accumulation after cell differentiation into cysts. In the latter, a portion or all of the population of cells has stopped dividing and is increasing in cell size.

The term "specific growth rate" refers to a quantitative measure of mass increase per unit of time. It should be qualified as to which growth phase its measurement encompasses to facilitate comparison across microalgal species and across studies.

Specific growth rate measured during active cell division that takes place prior to cell differentiation, also referred to as the "log" phase or "logarithmic growth" phase or "active growth" is distinct from that measured during a "resting", "non-vegetative growth" encystment phase, wherein individual cells stop dividing but can enlarge and increase in mass.

"Fed-batch fermentation" refers to a fermentation where one or more nutrients are supplied to the bioreactor during cultivation and in which the product remains in the bioreactor until the end of the fermentation run. In some cases a volatile or gaseous product can be removed in part during the fed-batch fermentation run.

A "product of interest" is a substance synthesized by a cell. Examples of a product of interest include, but are not limited to, proteins, lipids, carbohydrates, biogases, volatile materials, sugars, amino acids, isoprenoids, terpenes, or precursor thereof. Such substances may be synthesized constitutively by the organisms throughout their growth and the amount of the substance in the culture may increase simply due to an increase in the number of organisms. Alternatively, the synthesis of such substances may be induced in response to culture conditions or other environmental factors, for example, nitrogen starvation or elevated ammonium levels.

The amount of a product of interest accumulated over time relative to the culture volume and relative to their original amount is considered as "product accumulation" that can be measured by specific productivity.

The term "Chlamydomonadales" refers to the order of green algae that includes taxa formerly placed in Volvocales and Dunaliellales and as typified by *Chlamydomonas* (Lewis and McCourt 2004). Members of the order Chlamydomonadales have life cycles with distinct cell types for vegetative reproduction, resting phases and sexual reproduction.

The term "*Haematococcus*" refers to a group of unicellular microalgae that generally live in fresh water or, more recently have been isolated from a harsh saline environment (Chekanov et al. 2014) and are exemplified by species and strains of *H. pluvialis* and *H. lacustris* and those listed in algaebase (see, world-wide website: algaebase.org/), including those in public and private culture collections. *Haematococcus* is a genus of microalgae classified in the Eukaryota domain, Viridiplantae kingdom, Chlorophyta phylum or division, Chlorophyceae class, Chlamydomonadales order, and Haematococcaceae family.

The term "*Chlamydomonas*" refers to a genus of microalgae classified in the Eukaryota domain, Viridiplantae kingdom, Chlorophyta phylum or division, Chlorophyceae class, Chlamydomonadales order, and Chlamydomonadaceae family.

The term "conditions favorable to cell division" or "conditions favorable to vegetative growth" mean conditions in which cells divide at a pace such that an industrial production run is completed in about 60 to 168 hours, preferentially in less than 144, 120 or 96 hours, including a lag time of less than about 24 hours.

The term "cell differentiation" or "cellular differentiation" refers to different morphological changes in asexual reproduction, i.e., the conversion of vegetative cells to cyst cells. "Vegetative" cells, also referred to as zoospores or macrozooids, are biflagellate and motile with cells enclosed by an ovoid, ellipsoid, ellipsoid-cylindrical or nearly globose wall. "Cyst" cells (also referred to as "haematocyst" in *Haematococcus*), can be "immature cysts" that are spherical and immotile, lacking flagella, and develop into "mature cysts" or "aplanospores" that are resting cells that are spherical and immotile, lacking flagella, with a heavy resistant cell wall. These can germinate to vegetative cells with release of intracellular daughter cells or microzooids.

The term "co-culture", and variants thereof such as "co-cultivate", refer to the presence of two or more types of cells in the same fermentor or bioreactor. The two or more types of cells may both be microorganisms, such as microalgae, or may be a microalgal cell cultured with a different cell type. The culture conditions may be those that promote growth and/or propagation of the two or more cell types or those that facilitate growth and/or proliferation of one, or a subset, of the two or more cells types while maintaining cellular growth for the remainder.

The terms "cultivated" or "cultivation" or "culturing" refer to the purposeful fostering of growth (increases in cell size, cellular contents, and/or cellular activity) and/or propagation (increases in cell numbers via mitosis) of one or more microbial or microalgal cells by use of intended culture conditions.

The combination of both growth and propagation may be termed proliferation. Examples of intended conditions include, but are not limited to, the use of a defined medium (with known characteristics such as pH, ionic strength, and carbon source), specified temperature, oxygen tension, and growth in a fermentor or bioreactor. The term does not refer to the growth of microorganisms in nature or otherwise without intentional introduction or human intervention, such as natural growth of an organism.

The terms "fermentor" or "bioreactor" or "fermentation vessel" or "fermentation tank" mean an enclosed vessel or partially enclosed vessel in which cells are cultivated or cultured, optionally in liquid suspension. A fermentor or bioreactor of the disclosure includes non-limiting embodiments such as an enclosure or partial enclosure that permits cultured cells to be exposed to light or which allows the cells to be cultured without the exposure to light. The term "port", in the context of a vessel that is a fermentor or bioreactor, refers to an opening in the vessel that allows influx or efflux of materials such as gases, liquids, and cells. Ports are usually connected to tubing leading from the fermentor or bioreactor.

The term "fermenter" refers to an organism that causes fermentation.

The term "fixed carbon source" means a compound containing carbon that can be used as a source of carbon and/or energy by an organism. Typically, a fixed carbon source exists at ambient temperature and pressure in solid or liquid form.

The term "organic acid" refers to one or more molecules that are organic compounds with acidic properties. The most common organic acids are the carboxylic acids. A "carboxylic acid" contains a carboxyl group distinct from sugar carbohydrates such as glucose commonly used in algal fermentation. Acetic acid is a two-carbon carboxylic acid, $CH_3COOH$, commonly used in chemical manufacturing. In contrast the organic salt sodium acetate, $CH_3COONa$, is the trihydrate sodium salt of acetic acid. Propionic acid (propanoic acid) is a carboxylic acid with the chemical formula $CH_3CH_2COOH$. The anion $CH_3CH_2COO-$ as well as the salts and esters of propionic acid are known as propionates (or propanoates). Other such acids can include, but are not limited to, citric, fumaric, glycolic, lactic, malic, pyruvic, and succinic acids.

"Sugar acids" and "chlorogenic acids" are also organic acids and can include, but are not limited to, glucuronic, galaturonic and other uronic acids, and ferulic, with a carboxylic acid functional group such as obtained in lignocellulosic derivatives. Organic acids can be used alone or in combination, such as in combinations that may occur naturally in lignocellulosic derivatives.

The terms "heterotrophic conditions" and "heterotrophic fermentation" and "dark heterotrophic cultivation" or "dark heterotrophic culture" refer to the presence of at least one fixed carbon source and the absence of light during fermentation.

The terms "isoprenoid" or "terpenoid" or "terpene" or "derivatives of isoprenoids" refer to any molecule derived from the isoprenoid pathway with any number of 5-carbon isoprene units, including, but not limited to, compounds that are monoterpenoids and their derivatives, such as carotenoids and xanthophylls. The isoprenoid pathway generates numerous commercially useful target compounds, including, but not limited to pigments, terpenes, vitamins, fragrances, flavorings, solvents, steroids and hormones, lubricant additives, and insecticides. These compounds are used in products for food and beverages, perfumes, feed, cosmetics, and raw materials for chemicals, nutraceuticals, and pharmaceuticals.

The term "carotenoid" refers to a compound composed of a polyene backbone which condensed from five-carbon isoprene unit, "carotenoid" can be an acyclic, or one (monocyclic) or two cyclic and can be terminated by cyclic end-groups of the number (bicyclic). The term "carotenoid" may include both carotenes and xanthophylls.

A "carotene" refers to a hydrocarbon carotenoid. "Xanthophylls" are oxygenated carotenoids. Modification of pyrophosphate and phosphate groups of isoprene derivatives include oxidations or cyclizations to yield acyclic, monocyclic and bicyclic terpenes including, but not limited to, monoterpenes, diterpenes, triptperpenes, or sequiterpenes.

The terms "conditions favorable to carotogenesis" or "carotogenesis trigger" mean conditions in which cells accumulate carotenoids. These conditions can occur solo or as a combination of conditions and can be substituted for each other. A condition can occur intrinsically during the culture process or occur extrinsically and be imposed on, or supplied to, the culture, or be a combination thereof. The conditions can be chemical, biological, and physical in nature.

The term "microorganism" refers to microscopic unicellular organisms, including, but not limited to, microalgae. The microorganisms usable in the fermentation according to the present invention can include, but is not limited to, mutants, naturally occurring strains selected for a specific characteristic, or genetically engineered variants of a naturally occurring strain.

The term "microalgae" refers to a eukaryotic microorganism that contains a chloroplast, and optionally is photosynthetic, or a prokaryotic microorganism capable of being photosynthetic. Microalgae include, but are not limited to, obligate photoautotrophs, which are incapable of metabolizing a fixed carbon source as energy, and obligate or facultative heterotrophs, which are capable of metabolizing a fixed carbon source. Microalgae as obligate heterotrophic microorganisms include those that have lost the ability of being photosynthetic and may or may not possess a chloroplast or chloroplast remnant. Microalgae can divide to produce populations of cells and can be scaled-up or enter a production phase to produce biomass, a process that can be continued indefinitely until a maximum productivity is achieved.

The term "recombinant" when used with reference to a cell, nucleic acid, protein, or vector, indicates that the cell, nucleic acid, protein or vector, has been modified from its natural state. For example, a recombinant cell comprises an exogenous nucleic acid or protein or the alteration of a native nucleic acid or protein, or is derived from a cell or organism or microorganism so modified.

The terms "robust" or "robust culture", in the context of selected strains or lines of a species, refer to a population of algae that contain a desired phenotype and equal or greater growth characteristics, especially under heterotrophy, compared to the original strain. Maintaining the robust growth characteristic is highly problematic when using mutagenesis and chemical selection to obtain mutants with increased pigment content.

In some embodiments of the instant invention, novel selections and selected subpopulations resulting from methods that do not rely on mutagenesis for generating mutants are used to retain the robust growth characteristics along with the increased pigment content or other product yield under heterotrophy.

Heretofore, the provision for sustained rapid heterotrophic cell growth in a short timeframe suited for typical commercial fermentation cycles has not been recognized as a crucial factor for facultative heterotrophic microorganisms using organic acids as their sole source of fixed carbon.

A preferred embodiment of the invention provides a method that enables manufacturing biomass from a cell of the order Chlamydomonadales or a product of interest produced by a cell of the order Chlamydomonadales.

In certain embodiments, the instant invention provides methods that are used with the spore forming Chlamydomonadales or other microorganisms that have similar morphological or physiological responses to nutrient deprivation or sensitivity to elevated salt concentrations during dark fermentation culture that result in cessation of vegetative growth and thereby limit product formation.

Advantageously, the methods of the instant invention additionally enable co-culture with different cell types, which can include different microalgal species that do not require organic acids for heterotrophy but can preferentially utilize, and thus mitigate, accumulation of high levels of ammonium or other metabolites for rapid vegetative growth.

In preferred embodiments, the instant invention pertains to improved and cost effective dark heterotrophic fermentation methods. In certain embodiments, the invention provides the use of a cell belonging to the order Chlamydomonadales and other organic acid requiring microbial cells.

In preferred embodiments, the methods of the instant invention are directed to enabling a heterotrophic cell to achieve a specific growth rate for a period of time suited to industrial manufacturing. Advantageously, the methods of the instant invention can be practiced using equipment that is commercially available.

In certain embodiments, the instant invention provides a cell belonging to the order Chlamydomonadales which provides heterotrophic fermentation for industrial production of an isoprenoid or derivatives of isoprenoids and biohydrogen. The isoprenoids produced by the methods of the instant invention include, but are not limited to, pigmented isoprenoids, colorless phytoene, or derivative isoprenoid that can be produced by interruption or redirection of carbon flux.

In a preferred embodiment, the cell of the invention provides faster production, such as faster biomass, pigment or isoprenoid production. In another embodiment, the instant invention provides cells that exhibit commercial scale biogas production and recombinant molecule production, which cells function effectively and economically under fermentation conditions.

In a certain embodiments, a heterotrophic cell of the order Chlamydomonadales is provided, which cell accumulates a pigment in the vegetative phase without cell differentiation and when cultured according to a method disclosed herein and demonstrates an active native non-mevalonate MEP pathway. For example, when supplied with a non-limiting organic acid, the cell provided by the instant invention is primed for carbon flux through pathways to added sinks, advantaged without interference from photosynthesis. In certain embodiments, the cell provided by the invention belongs to order Chlamydomonadales and is a heterotrophic cell that is achlorophyllic and non-photosynthetic.

In some embodiments, the invention provide methods that enable the generation of heterotrophic biomass, from a facultative heterotrophic Chlamydomonadales cell with an altered isoprenoid profile. In certain embodiment, using methods of the instant invention the biomass can be generated in a fermentor at a high growth rate and over a relatively short period meaningful for industrial application.

Various strategies available for producing recombinant cells for isoprenoid synthesis can be adopted to engineer heterotrophic cells for altered isoprenoid production.

The cells and the methods of the instant invention and described herein 1) provide high specific growth rates over the duration of the production period;

2) use organic acids to manage salt toxicity allowing extended conditions favorable to vegetative growth;

3) use urea to further manage salt toxicity;

4) eliminate the requirement for cellular differentiation to effect product accumulation;

5) accumulate high product yields in the absence of light;

6) accumulate high product yields in the absence of nutrient deprivation; and 7) the methods employ improved strains and cell lines for high yield, high quality and secure fermentation.

The heterotrophic microalgal product, either extracted or the biomass, can be used for animal feed, human nutrition and nutritional supplements, personal care, colorant, flavor or fragrance, bioenergy, crop protection, or for chemical modification prior or post product formation.

Using the methods of the instant invention, the myriad of critical advantages gained by large-scale fermentative algal culture can be realized for the Chlamydomonadales mediated production of isoprenoids, carotenoids, biogas and other products.

The improved methods of the instant invention described herein allow for uninhibited growth for longer duration such as 48, 72, 96, 120 hours or more, and at high cell density.

The methods of the instant invention avoid the requirement for dilution of culture and the requirement of sodium acetate to feed carbon. Both of these "requirements" cause salt build up and inhibition of growth and are avoided in the methods of the invention. Accordingly, in certain embodiments, the invention utilizes organic acid as the primary source of carbon throughout the fermentation. To avoid using nitrates as the nitrogen source and to minimize addition of salts, in some embodiments, organic nitrogen, including, but not limited to, urea, is used. In certain embodiments, the culture medium is devoid of nitrates as a nitrogen source and comprises urea.

In some embodiments, the increase in culture pH is balanced by addition of organic acid in a fed-batch manner as the carbon source without introduction of extra salt to the medium. Accordingly, in preferred embodiments, the culture medium is devoid of a salt of the organic acid used in the medium as a fixed carbon source.

Advantageously, the methods of the instant invention provide yields of about 110% to about 150% or up to about 250% or more pigment or precursor content when compared to the cultures cultivated according to methods currently used.

In some embodiments, the instant invention provides the use of indoor fermentation vessels for heterotrophy as described herein, which indoor fermentation offers a new solution for biosecurity for strains that are cultured phototrophically and outdoors at large volume. The use of fermentation tanks, especially tanks located indoors, can simplify regulatory approval of the industrial scale manufacture of recombinant products.

In certain embodiments, the methods provided herein can be used for the expression of recombinant proteins by culturing a microalgal cell including, but not limited to, *Haematococcus* spp., for example, *H. pluvialis; Chlamydomonas* spp., for example, *Chlamydomonas reinhardtii*; or a *Dunaliella* spp.

Use of monocultures in industrial applications is standard, notably for fermentation. In contrast, community ecology is found in nature to benefit photosynthetic algal production in ponds and raceways. While the conditions of heterotrophic fermentation might strongly discourage, but not preclude, introduction of faster growing bacteria to prevent their undesired dominance, the introduction of eukaryotes with more similar cell division frequencies as the target microalgae could be beneficial.

In some embodiments of the instant invention, eukaryotes are provided that require an alternative carbon or nitrogen source that can be withheld or supplied when needed to modify population dynamics in co-cultures. Accordingly, one embodiment of the invention provides a method of co-cultivating a cell belonging to the order Chlamydomonadales with a second microorganism.

Accordingly, a specific embodiment of the invention provides culturing a cell belonging to the order Chlamydomonadales to heterotrophically accumulate sufficient biomass and target compound over a minimal time period.

In preferred embodiments, the lag phase is effectively minimized or eliminated. In certain embodiments of the instant invention, the specific growth rate is no less than 0.6/day and is increased to 1.1/day or more and sustained for a period of time sufficient to produce growth whereby it is longer than about 24 hours, about 48, or about 72 hours or more.

In a particular embodiment, the specific productivity (qp) for a pigment is about 1.4 mg/L-hour and is increased to about 5.5 mg/L-hour or more. In another embodiment the total fermentation cycle time is about 72, about 96, or about 120 hours or about 144 hours or by any duration falling within the range of 24 hours to 144 hours or a duration that is economically justified.

In another embodiment, the instant invention enables the use of organic acids instead of organic salts like sodium acetate, thus avoiding the salt toxicity seen during heterotrophic fermentation of microorganisms that require organic acids as their source of fixed carbon. In some embodiments, use of sodium acetate is minimized or eliminated by replacement with an alternative fixed carbon source for metabolism and growth by the microorganism. Accordingly, the fixed carbon source used in the methods of the instant invention include, but are not limited to, a carboxylic acid, sugar acid, or chlorogenic acid. Non-limiting examples of a fixed carbon source include acetic, succinic, citric, fumaric, glycolic, malic, pyruvic, glucunoric, galacturonic, or proprionic acid. In certain embodiments, the organic acid used as a fixed carbon source can be derived from lignocellulosic biomass. Additional examples of a fixed carbon source are known to a person of ordinary skill in the art and such embodiments are within the purview of the invention.

The fixed carbon sources can be used alone or in a combination. Coordinately, in particular embodiments, sodium nitrate in the culture medium is replaced with a complex nitrogen source before or during culturing. Exemplary complex nitrogen sources considered useful in the invention include, but are not limited to, urea and hydrolyzed casein.

In certain embodiments, nitrates can be used as a nitrogen source in strains that are more salt tolerant or in some amounts with complex nitrogen source or a combination of nitrate and a complex nitrogen source.

In some embodiments, the culture medium contains sodium acetate. Sodium acetate can be used alone or with at least one other fixed carbon source. In preferred embodiments, the at least one other fixed carbon source is acetic acid.

In some embodiments, all of the sodium acetate and all of the at least one other fixed carbon source are provided to the microorganisms at the beginning of fermentation.

In other embodiments, the sodium acetate is provided at the beginning of the fermentation process and the at least one other fixed carbon source is provided at a predetermined rate over the course of the fermentation or at a rate triggered by pH set points. For example, in one embodiment, the at least one other fixed carbon source is provided when the pH of the fermentation medium reaches about 7.5 or about 8.5.

In some embodiments, sodium acetate is provided in the absence of the at least one other fixed carbon source for a first period of time, the at least one other fixed carbon source is provided at the end of the first period of time, and the microorganisms are cultured for a second period of time in the presence of the at least one other fixed carbon source.

In certain embodiments, the invention provides methods that do not require cell differentiation for accumulation of a product of interest during heterotrophic fermentation. For example, in certain embodiments, macrozooids accumulate carotenoids, isoprenoids, or terpenoids while remaining motile and biflagellate without the occurrence of encystment.

In further embodiments, the methods of the invention enable accumulation of high product yields in the absence of light. In certain embodiments, the conditions within the fermentor are such that the microorganisms generally do not photosynthesize during cultivation, nor is there any stage of operations where photoinduction is enabled by a purposeful or adequate exposure to light.

In certain embodiments, the invention also enables accumulation of high product yields in the absence of nutrient deprivation. For example, in certain embodiments, macrozooids accumulate carotenoids in the absence of nutrient deprivation, remaining motile and biflagellate, and encystment does not occur.

In even further embodiments, the invention provides a heterotrophic co-cultivation with at least one other microorganism. In preferred embodiments, the mutualism between two microalgal strains is described where accumulation of high levels of ammonium ($NH_4^+$, $NH_3$) or other metabolites that might otherwise inhibit cell division of one strain is mitigated by the other strain.

In certain embodiments, co-culture or co-cultivation is used as a strategy to promote proliferation of the target species. In a particular embodiment, co-culture is between a strain that requires organic acids as its fixed carbon source for heterotrophy and another strain that does not require organic acids for heterotrophy and can preferentially utilize ammonium or the other metabolite, including, but not limited to, ethanol, lactate, or formate that can accumulate under low oxygen.

The present invention further relates to generating and cultivating microorganisms suited for heterotrophically producing high yields of carotenoids and isoprenoid precursors or derivatives for biomass and products containing said microorganisms or said carotenoids and isoprenoid precursors or derivatives thereof.

The microorganisms of the invention can be selected or genetically engineered for use in the methods described herein. In some embodiments, heterotrophic fermentation of a member of the order Chlamydomonadales previously only cultivated photoautotrophically is provided.

In further embodiments, the invention provides improved strains that provide high productivity under dark heterotrophic fermentation.

In some embodiments, the instant invention provides heterotrophic cultivation of a genetically engineered organism.

In certain embodiments, the instant invention provides heterotrophic fermentation of a selected naturally occurring variant. According to the methods of the instant invention, the selection of a naturally occurring variant having high productivity can be performed by laser flow cytometry (FCM; used interchangeably with fluorescence activated cell sorting, FACS). Using methods of the instant invention, subpopulations of algae that have higher pigment content compared to the original population can be selected and isolated using FCM based on their ability to accumulate the target pigment more quickly compared to the original population. Recurring selection can be used to select strains with improved performance over time.

In further embodiments, the instant invention provides isolated and selected subpopulations of algae that accumulate precursor compounds, accompanied by a reduction in the levels of the natural endpoint compound further down the biosynthetic pathway. In preferred embodiments, the accumulating compounds are colorless antioxidant compounds including, but not limited to, phytoene and phytofluene. In some embodiments, these subpopulations are selected based on differential fluorescence using flow cytometry. Such subpopulations accumulate these colorless high value products at levels similar to the levels of the pigment the species accumulates naturally, as seen in cells with chemically-induced blockage of pigment biosynthesis. The methods of the instant invention provide direct selection performed at the correct stage for each species to increase the efficiency of recovering improved cell lines with superior industrial performance. In further embodiments, indirect correlative selection using Nile Red, or lipid stains are also provided.

In some embodiment, variants that lose chlorophyll and accumulate pigments are selected for fast accumulating and high accumulating pigments. In other embodiments, cells or populations are utilized, which cells and populations are identified by lack of phototaxic response to no longer be flagellated and, thus, are non-motile but still vegetative. Such cells are advantageous in fermentation systems because they are not susceptible to damage by the impeller like their flagellated counterparts.

Isoprenoids of the instant invention include, but are not limited to, carotenoid/xanthophylls such as astaxanthin, or colorless phytoene and phytofluene.

In some embodiments, the methods of the instant invention efficiently cultivate high producing genetically modified cells accumulating specific targets through an altered biosynthesis. In preferred embodiments, these targets are secondary metabolites including, but not limited to, lycopene or zeaxanthin. In further preferred embodiments, these are isoprenoids obtained by expression of an added synthase gene/enzyme.

The methods provided herein enable the use of cells that are easily manageable, easily cultivable with faster crop cycle times, production all during the year and across geographies, and from which the desired product can be obtained economically in high yields.

The methods used in harvesting and further processing the biomass for isolating a product of interest are well known in the art. For example, some methods of harvesting include, but are not limited to, centrifugation, flocculation, and filtration for dewatering and headspace entrapment and sparging or removal for volatile compounds or biogas. Some methods of extraction useful in the instant invention include, but are not limited to, extractions in organic solvents, in edible oil, and by pressurized fluid and gas.

In certain embodiments the heterotrophically produced biomass is used directly or as an admixture in animal and fish feed. For example astaxanthin-containing biomass is used for fish feed, and recombinant *Chlamydomonas* biomass is used in poultry feed.

In other embodiments the isoprenoids are extracted. In some embodiments, astaxanthin is extracted as described in the U.S. Pat. No. 6,022,701. A myriad of applications for astaxanthin include those described in the art, for example, in Ambati et al. 2014, Tables 4 and 5.

In further embodiments of the invention, methods for improved cultivation of cells under mixotrophic conditions are provided. In some embodiments, it is desirable that light be supplied to increase the growth rate of the cells beyond that of heterotrophic conditions. For example, in *H. pluvialis* the specific growth rate under mixotrophic conditions is 2.5 fold higher than the specific growth rate under heterotrophic conditions. In *C. reinhardtii* the specific growth rate under mixotrophic conditions is 1.8 fold higher than the specific growth rate under heterotrophic conditions.

Advantageously, the present invention, for example, via reduced salt build up, provides for extended log phase growth in mixotrophic systems. This may be particularly advantageous for increasing pigment accumulation without cell differentiation beyond the already high levels seen under heterotrophic conditions. A further advantage of mixotrophic growth is that dissolved oxygen levels in the culture medium will be easier to maintain as the cells will be producing oxygen as they fix $CO_2$ using light.

In certain embodiments, the invention provides methods of fermentation that do not require differentiation of the cultured cells for massive accumulation of a product of interest.

In other embodiments, the invention also allows significant biomass, carotenoid, and biogas accumulation in the dark for measurably high specific growth and productivity rates to enable short cycle times. In further embodiments, the invention provides new strains that are selected to create even more productive heterotrophs to maximize product levels for the lowest operation costs. Thus, fermentation methods and cells are described that provide higher yields by a simple process in the dark without the need for cell differentiation.

The methods of the invention provide culturing a microalgal cell, for example, a genetically modified algal cell, in a secure heterotrophic platform which transforms algal manufacturing for significant economic gain.

The methods of the invention provide:
1) faster manufacturing cycles;
2) simpler production logistics for biomass or a product of interest;
3) reduced operating costs to compete with chemical synthesis;
4) faster industrial scaling using equipment and infrastructure standard for microbial fermentations;
5) year round production, indoors, independent of geographic location, and without the problems associated with outdoor or open operations;
6) significantly increased inventory and access to much larger markets; and
7) large-scale economic production of multiple species, including those used as hosts for recombinant molecules under GMP and regulatory restrictions.

Examples of general principles and methods for heterotrophic algae cultivation, such as establishing axenic cultures, using a seed train with a plurality of passages prior to addition of final inoculum, the design of the fermentors that prevent illumination of the microalgae, and cultivation until harvest or partial harvest, are described in the art, for example, in U.S. Pat. No. 8,278,090, which is incorporated herein by reference in its entirety.

In particular embodiments, the inoculum added to the fermentor can be produced by cultivation of the Chlamydomonadales in the dark for at least one passage prior to its addition to the fermentor, or by prior cultivation in the dark for a plurality of passages, e.g., 2 passages, 3 passages, 4 passages, or 5 or more passages.

In certain embodiments, after cultivation of the microalgae in the fermentor for a period of time in the dark, all or a portion of the microalgae can be transferred to a further fermentor vessel, where the microalgae can be further cultured for a period of time, wherein the further vessel prevents exposure of the microalgae to light. In practical terms, members of the Chlamydomonadales that are not previously grown in dark fermentation but reported as having a mixotrophic nature, for example, various snow algae, are candidates for the practicing the invention.

Harvest or separations, biomass processing, handling of intact biomass as a product, cellular lysis, product extraction, supercritical fluid processing, or other isolation and purification of products may be done by using any methodology known to a person skilled in the art. Non-limiting examples of such techniques are described, for example, in U.S. Pat. Nos. 8,278,090 and 7,329,789, both of which are incorporated by reference.

Non-limiting examples of product recovery include the separating different target compounds by use of a fractional distillation column. Further non-limiting examples for concentration, drying, powdering, grinding in preparation for extraction or use as a biomass for animal and fish feed, are described, for example, in U.S. Pat. No. 6,022,701 and EU patent application publication no. EP1501937, both of which are incorporated herein by reference. US patent application publication no. 20120171733 describes various means for cell lysis that are incorporated herein by reference.

US patent application publication no. 20090214475, which is incorporated herein by reference, describes soft wall mutant strains of *Haematococcus pluvialis* for improving the extractability and bioavailability of natural astaxanthin, and their use in animal feed, human dietary supplements, pharmaceuticals, and foods.

Methods of the instant invention provide typical microbial growth curves or growth cycles using a fermentor. For example, using methods of the instant invention, an inoculum of cells when introduced into a medium is followed by a lag period before cell growth or division begins. Following the lag period, the growth rate increases steadily and enters the log, or exponential, phase. Specific growth rate, defined as $\mu=\ln(X/X_i)/t$, where X is the final dry cell concentration, $X_i$ is the initial dry cell concentration and t is the cultivation time, is measured during this period. The exponential phase is followed by slowing of growth (cell division) due to nutrient depletion and/or increases in inhibitory substances. When growth stops the cells enter a stationary phase or steady state. According to methods of the instant invention, specific productivity (qp) is measured over the full time course of lag, log, and stationary phase until harvest; qp= (X)*(P)/t, where X is the harvest dry weight, P is the percent of product on a dry weight basis, and t is the cultivation time.

The methods of the instant invention provide measurement of the relative pigment content in individual cells by FCM. According to the instant invention, FCM can also be used for isolating cells having pigment contents above average when compared to the original population to produce a population of cells containing increased pigment content in the newly created subpopulation. Further according to the methods of the instant invention, FCM, using the fluorescein diacetate (FDA) stain to differentiate between vegetative cells, immature cysts, and mature cysts, can also be used to identify and isolate cells that accumulate pigments and remain motile to generate a new subpopulation of cells that accumulate pigment faster than the original population. These methods are non-limiting and can be applied with slight modifications to select any cell type (motile or cyst) with various pigment characteristics, for example, high astaxanthin, lycopene, phytoene, for eventual growth under heterotrophy.

In certain embodiments of the instant invention, a genetically engineered microorganism is heterotrophically cultivated to enhance traits such as the production of biohydrogen, isoprenoid, or recombinant molecule, to modify the properties or proportions of components generated by the microorganism, or to improve or provide de novo growth characteristics.

Methods for genetic engineering of *Haematococcus* spp. (Sharon-Gojman et al. 2015), *Dunaliella* spp. (Feng et al. 2014), and *Chlamydomonas* spp. (Lauersen et al. 2013; Scaife et al. 2015; Scranton et al. 2015) are well documented and incorporated by reference herein. Promoters, cDNAs, and 3'UTRs, as well as other elements of the vectors, can be generated through cloning techniques using fragments isolated from native sources (see for example Sambrook et al. 2001; and U.S. Pat. No. 4,683,202). Alternatively, elements can be generated synthetically using known methods (see, for example, Stemmer et al. (1995)). Selectable markers and reporters or mutants that are restored upon transgene insertion are also well known in the art. Certain promoters useful in algal culture conditions are described for example in US patent application publication no. 20090317878, which is incorporated herein by reference, including those use for inducible expression such as in response to a stimulus like ammonium or carbon dioxide.

A recombinant nucleic acid molecule or polynucleotide can be introduced into plant chloroplasts or nucleus using any method known in the art. A polynucleotide can be introduced into a cell by a variety of methods that are well known in the art and determined, in part, based on the particular host cell. US patent application publication no. 20090317878, which is incorporated herein by reference, describes use of intergenic IGS sequences in microalgae for nuclear transgene expression. Further, a genetically engineered microorganism, such as a microalgae, may comprise and express one, two, or more exogenous genes, notably if it is in a transgenic plastid. U.S. Pat. Nos. 7,135,620 and 7,618,819 incorporated herein by reference, describe chloroplast expression vectors and related methods.

As such, methods for synthesizing a product of interest are provided herein. The methods comprise the steps of:

providing a culture medium comprising an organic acid as a fixed carbon source;

providing a microalgal cell that produces the product of interest, wherein the microalgal cell is a facultative heterotroph;

culturing the microalgal cell in the culture medium in the dark to produce a microalgal culture from the microalgal cell;

isolating the microalgal cells from the microalgal culture before the cells in the microalgal culture undergo cell differentiation; and purifying the product of interest from the microalgal culture.

The product of interest can include, but is not limited to a microalgal biomass comprising the microalgal cells, pigment, terpene, recombinant molecule, biogas, or a precursor thereof. The pigment can include, but is not limited to, a carotenoid, isoprenoid, or precursor thereof, for example, astaxanthin, lutein, lycopene, zeaxanthin, canthaxanthin, beta-carotene, phytofluene, or phytoene.

The terpene or a precursor thereof can include, but is not limited to, pinene, limonene, or geranylgeranyl pyrophosphate.

The recombinant molecule of interest can be a heterologous protein or a dsRNA.

In preferred embodiments, the methods described herein, when used to synthesize a pigment in a facultative heterotrophic algal cell, produce the pigment at a specific productivity rate of at least 0.063 mg/L-hour.

Also, the methods described herein provide for longer period of vegetative growth in a microalgal cell, for example, a vegetative growth period of between four days to a week, particularly, 48, 72, 96, 120 or 144 hours. The methods of the instant invention provide heterotrophic growth and synthesis of the product of interest throughout the step of culturing, for example, over 48, 72, 96, 120 or 144 hours, and wherein the step of culturing is performed under a fed-batch fermentation.

As mentioned above, unlike conventional methods where the product of interest is synthesized during cell differentiation phase under nutrient depletion conditions, the methods of the instant invention provide a synthesis of a product of interest under nutrient replete conditions throughout the vegetative growth of the culture.

Also, unlike conventional methods where the product of interest is synthesized during the cell differentiation phase under conditions of nutrient depletion and elevated light, the methods the instant invention provide a synthesis of a product of interest under nutrient depletion conditions throughout the vegetative growth of the culture without the requirement of light.

The methods of the instant invention provide algae produced in closed culture systems to exclude contamination and are therefore of high quality suited for a variety of novel animal and human uses. The closed fermentation systems of the instant invention also offer large quantities at lower cost, being produced at higher densities and faster growth rates within a short cycle time of merely days. In preferred embodiment of the instant invention, the algae are harvested before encystment and produced under nutrient replete conditions under darkness. Therefore, their typical compositional analysis differs substantially from encysted differentiated cells or cells that are stressed by light for pigment formation.

In certain embodiments the methods of the instant invention provide a substantially new profile of pigmented biomass with high protein and low ash composition (along with vitamins and minerals in the biomass) for a product that confers nutritional or coloration benefits for use for animals and humans. These nutrition benefits are comparable to those provided by fish-derived ingredients delivered while serving as a feed colorant or pigment supplement. By virtue of this composition, the compositions produced using the methods of the instant invention are also attractive in meal replacement beverages or nutrient supplements delivered as a carotenoid additive.

In some embodiments, because these algae are produced in closed culture systems to exclude contamination and to attain high densities in short periods of time while in the vegetative state, the algae cultures of the instant invention can serve to seed photobioreactors or raceways, lighted by solar radiation or artificial illumination, as part of a seed train or production cycle.

In certain embodiments, the methods of the instant invention provide a substantially new profile of pigmented biomass by virtue of its composition, which biomass is attractive as personal care and cosmetic ingredients delivered as, for example, a carotenoid-containing lysate or extract.

In certain embodiments of the instant invention, the culture medium comprises urea as a primary source of nitrogen.

The step of isolating and purifying the product of interest may comprise one or more steps of drying, grinding, lysing, or extracting the microalgal cell.

Also provided herein, is a method of identifying and isolating a microalgal cell that is suitable for synthesis of a product of interest. The method comprises the steps of:
 a. culturing a microalgal strain under at least partially heterotrophic conditions to produce microalgal cells,
 b. identifying a non-mutagenized microalgal cell having a preferred characteristic, when grown in heterotrophic conditions, relative to the microalgal strain from which the microalgal cells are produced, where the step of identifying is performed using a fluorescence activated cell sorting technique and/or a phototaxic response,
 c. isolating the non-mutagenized microalgal cell having the preferred characteristic.

The step of culturing can be performed under mixotrophic conditions, at least for a portion of the culturing step.

In many embodiments of the instant invention, various characteristics can be pursued to identify a cell, including, but not limited to, an increased synthesis of a product of interest by the microalgal cell, the absence of flagella in the microalgal cell, achlorophyllic or non-photosynthetic variant.

Accordingly, the instant invention provides cells having a desirable character compared to a parent microalgal culture.

The following examples are provided to describe the invention in further detail. These examples serve as illustrations and are not intended to limit the invention.

Example 1—Establishment of Heterotrophic Strains and Cultures

This example is directed to novel heterotrophic cell types that are cultivated with conditions favorable to vegetative growth and making product using the method of the invention. Cells of *Haematococcus* are isolated as environmental samples or obtained from culture collections such as UTEX 2505 obtained from the Culture Collection of Algae at the University of Texas (Austin, Tex., USA). Cells can include isolates with higher salt tolerance such as photosynthetic *Haematococcus pluvialis* strain BM1 (Chekanov et al. 2014). Cells can also be obtained from commercial-scale photosynthetic production cultures. Germination of cysts or spores, if present, takes place under conditions favored to produce motile cells that divide and subdivide to produce a culture containing green motile cells. Use of an inverted microscope is effective to identify the life cycle stage (vegetative, immature cyst, cyst). To reduce initial contaminant load the culture is centrifuged at 200 g for 1 minute to selectively pellet heavy cells including algae and contaminants. Immediately after centrifugation the media is removed, replaced with sterile media, centrifuged at 1000 g for 1 minute and the motile cells are allowed to swim to a light source above the centrifuge tube. The motile cells are collected, transferred to a new tube, and centrifugation is repeated until the supernatant contains few organisms other than the target organism. This contaminant-reduced culture is then treated with antibiotics (ampicillin 50 mg/L and cefotaxamine 250 mg/L) for 24 to 48 hours to further reduce the amount of bacteria, then diluted and target single cells are sorted using FCM into 96 well plates containing 200 μL of a basal growth medium as known in the art, for example, Guilliard's F/2 medium (modified for fresh water also with nitrate replaced by urea), with the same antibiotics.

Next, the method for strain selection is implemented. The 96-well plate is incubated under phototrophic conditions 20 μE light at 25° C. for 1 week; 10 μL of the culture is transferred to 200 μL of F/2 base media above supplemented with 20 mM sodium acetate and 0.16 g/L yeast extract (no antibiotics). This culture containing acetate is incubated again under 20 μE light (mixotrophic) for a week to identify axenic cultures using an inverted microscope. Axenic cultures (10 μL) are transferred to 200 μL of F/2 base media above supplemented with 20 mM sodium acetate and 0.16 g/L yeast extract (no antibiotics) in the dark to confirm the lack of other organisms and to begin to adapt to heterotrophic conditions. After rendering the cultures axenic, several weeks of weekly selection are performed, at 5 mL volume in 50 mL flasks, to specifically select the novel phenotype of heterotrophic motile cell types in very low nutrient condition. A motile cell type is isolated away from cysts based on the ability to be phototaxic when a light source is provided at the top of a vessel. This cell type retains its variant phenotype for numerous generations under heterotrophic conditions with robust growth and is assigned a new strain number. Populations subsequently generated are improved strains characterized by fast growing motile cells that are recalcitrant to form cysts under stress. For other Chlamydomonadales, cells of *Chlamydomonas* and *Chloromonas* are isolated as environmental samples as is known in the art or obtained from culture collections such as *Chlamydomonas* Resource Center CC-125 or 137c, or UTEX SNO4. These can be used as original cell types or used in generation of non-mutagenized variants suitable for preferred performance in heterotrophic conditions (see, for example, EXAMPLE 13); or as cell types recombinant for trophic conversion such as for *Dunaliella* (Chen et al. 2009). Similarly, cells of *Chlamydocapsa*, which has been previously only cultivated photoautotrophically (US patent application publication no. 20100316720), are obtained such as from CCCryo 101-99, IBMT strain collection, rendered axenic, and adapted to heterotrophic conditions as above using corresponding culture medium (3N-BBM) with a pH of 5.5 from 14° C. to 15° C.

Example 2—Media Composition and Temperature for Heterotrophic Growth

Medium components that produce the greatest increase in growth are identified for various species. This is performed at flask level initially, with a starting basal medium, and uses acetate as the fixed carbon source because the frequent (hourly) manual acetic acid additions are too labor intensive and would require round the clock day care. Using *H. pluvialis* KAS1601 as one example, the use of urea as a nitrogen source produced 40% increase in growth over $KNO_3$ and 28° C. temperature produced 57% increase over 25° C., giving an overall 2.2-fold increase in OD750 after the same time point before stationary phase begins. Specifically, the preferred nitrogen source is determined using heterotrophic flask growth media at 25° C. consisting of a baseline medium of 1.6 g/L sodium acetate, 0.16 g/L yeast extract, 1.76 mM nitrogen (0.88 mM urea or 1.76 mM $KNO_3$), 0.05 g/L magnesium sulfate heptahydrate, 0.05 g/L calcium chloride dihydrate, 0.02 g/L potassium phosphate, 0.01 g/L iron-EDTA, 0.0063 g/L iron chloride hexahydrate, 22 mg/L tetrasodium EDTA, 0.3 mg/L cobalt sulfate, 6 mg/L manganese sulfate, 0.8 mg/L zinc sulfate, 0.2 mg/L copper sulfate, 0.7 mg/L ammonium molybdate, 0.4 mg/L boric acid, 0.4 mg/L thiamine hydrochloride, 2 µg/L biotin, and 2 µg/L vitamin B-12. OD750 measurements are taken using a spectrophotometer. On day 2 there is no difference in OD750 of urea and $KNO_3$ grown cultures but by day 4 cultures using urea have a 40% higher OD750 compared to $KNO_3$ cultures. A preferred temperature is determined using the preferred nitrogen source (urea) at 25° C., 28° C., and 31° C. Under these conditions with no adaptation going directly from 25° C., motile cells do not proliferate at 31° C. OD750 measurements are taken using a spectrophotometer to monitor growth. On day 3 there is no difference in 25° C. and 28° C. grown cultures; however, by day 5 the cultures at 28° C. have a 57% higher OD750 compared to 25° C. cultures. Similar methods for determination of medium composition suited for heterotrophic growth for other strains are done as is known in the art. For *Chlamydomonas*, the same temperatures are tested in flask, with a substitution of 1.6 g/L sodium acetate with 0.4 g/L sodium acetate and the preferred nitrogen source determined as above (urea). It is understood that other medium components can be modified or excluded or added using standard multivariate growth studies, as is known in the art. This includes the use of various organic acids as carbon source, and the organic acid can be one type or more than one type combined such as may occur in lignocellulosic derivatives.

Figure 2:
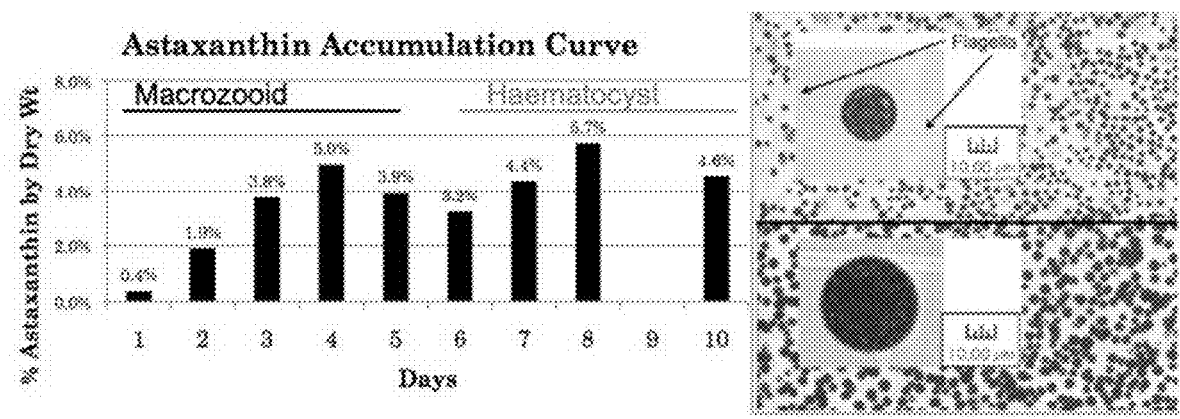
FIG. 2. Left. Example of an isoprenoid accumulation curve of a selected microalgal isolate. Vegetative macrozooid (motile, biflagellate) cells can accumulate high levels of pigmented isoprenoid, astaxanthin, in just a few days. If allowed to differentiate into haemotocysts, they may accumulate even higher amounts of product. Right top: Red motile flagellated macrozooid cell and population with accumulated pigment in heterotrophic culture. Right bottom: Typical red immotile unflagellated haematocysts in phototrophic culture. Note the enlarged cell size, which accounts for the increase in cell mass with cessation of cell division. Commercial producers must employ stress in light over at least 7-10 days to obtain cysts.
Figure 3:
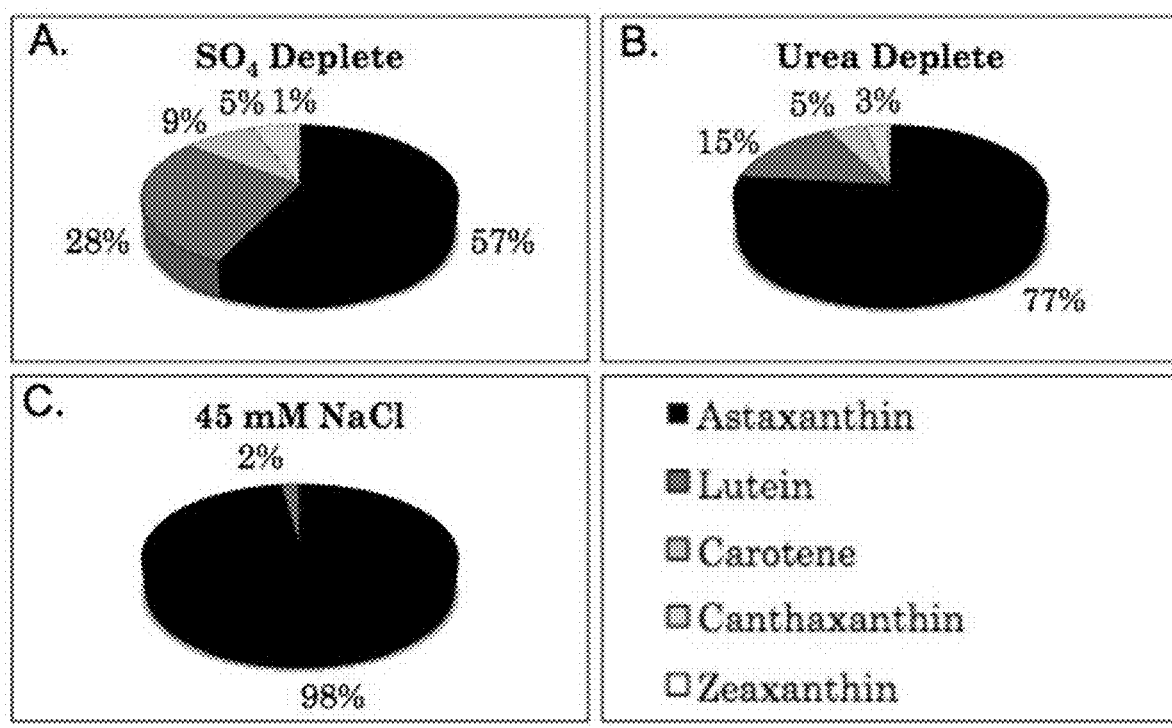
FIG. 3. Examples of varying pigment profiles 3 days after carotenogenesis trigger showing the relative amounts of each carotenoid of the total carotenoids. A: $SO_4$ deplete. B: Urea deplete; the carotenoid profile is also similar to excess ammonium accumulation. C: 45 mM NaCl added.
Figure 4:
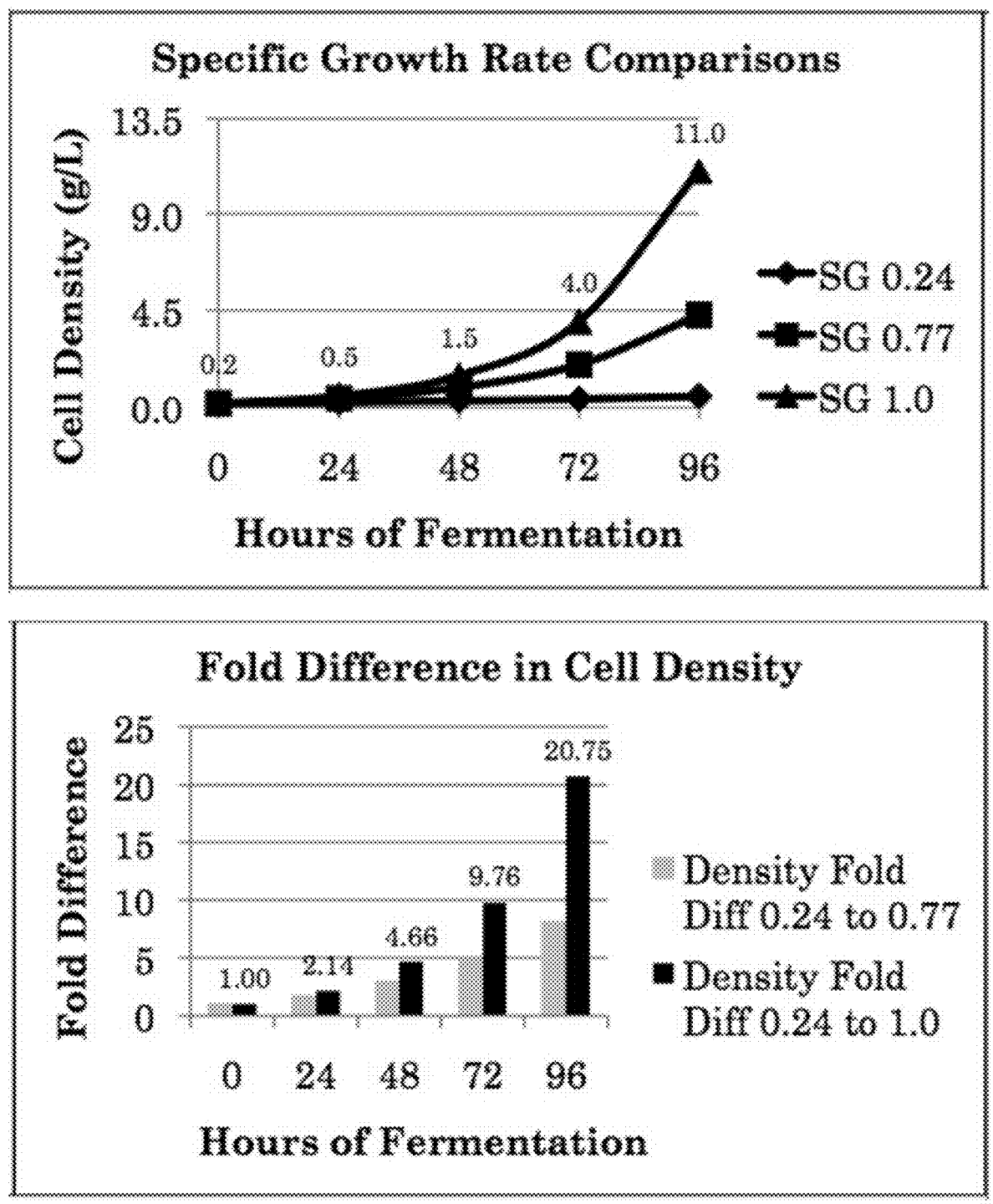
FIG. 4. Heterotrophic biomass accumulation during vegetative growth on organic acids over time with 0.2 g/L initial biomass for various specific growth rates according to the method of the instant invention. A: A specific growth rate of 0.77/day (square line, from the steps described in Example 5) and 1.0/day (triangle line, from the steps described in Example 6) by the method of the instant invention compared to 0.24/day (diamond line, the highest reported prior art value). B: Fold difference in biomass accumulation by vegetative growth using the method of the instant invention over time is compared to prior art growth rate. A small change in specific growth rate has huge effects on cell density. Specific growth rate values of 0.24/day to 0.77/day represent a 3.2-fold increase in specific growth rate; at 96 hours the yield is a 8.1-fold higher cell density. Specific growth rate values of 0.24/day to 1.0/day represent a 4.2-fold increase in specific growth rate; at 96 hours the yield is a 20.75-fold higher cell density.

Example 3—Heterotrophic Media Composition and Pigment Production by Macrozooid Cells This example employs strains selected for preferred growth under heterotrophic conditions. Using *Haematococcus pluvialis* KAS1601 as an example for describing the seed train, nine 500 mL vegetative heterotrophic cultures of *H. pluvialis* were grown in batch culture in a 1 L flask at 25° C. with shaking at 100 rpm for sufficient time to be well into the growth phase but before entering stationary phase, as measured by cell densities having an OD750 of 0.15 in early growth phase and increasing to an OD750 of about 0.6 in late growth phase. Flask growth media consist of 0.16 g/L yeast extract, 0.11 g/L urea, 0.05 g/L magnesium sulfate heptahydrate, 0.05 g/L calcium chloride dihydrate, 0.02 g/L potassium phosphate, 0.01 g/L iron-EDTA, 0.0063 g/L iron chloride hexahydrate, 22 mg/L tetrasodium EDTA, 0.3 mg/L cobalt sulfate, 6 mg/L manganese sulfate, 0.8 mg/L zinc sulfate, 0.2 mg/L copper sulfate, 0.7 mg/L ammonium molybdate, 0.4 mg/L boric acid, 0.4 mg/L thiamine hydrochloride, 2 µg/L biotin, and 2 µg/L vitamin B-12. Additionally, the flask medium contains either 2.78 g/L Tris base with 1.15 mL/L acetic acid or it may initially contain 1.6 g/L sodium acetate to allow for low maintenance growth of low density flask cultures. The cultures are concentrated by centrifugation at 3000 g for 5 minutes or used as is. The microalgal cells (FIG. 1-10) are transferred to 3 L of fermentor heterotrophic growth media (same as flask heterotrophic media supplied with 0.7 g/L Tris base and an initial 0.29 mL/L acetic acid or optionally a one-time 0.4 g/L sodium acetate) in a 14 L fermentation vessel (New Brunswick BioFlo 3000; FIG. 1-30) with an initial biomass density of 0.2 g/L. The 3 L fermentation culture is incubated at 28° C. with gas exchange provided by 3 L/min sparged air and a pitched blade impeller at 100 to 150 rpm at pH 7.8. Using BioCommand Software, peristaltic pumps, and head plate ports the pH is maintained at pH 7.8 to 7.3 throughout the duration of the fed-batch fermentation with pH-triggered additions of 10% acetic acid (FIG. 1, embodiment 20) supplied at 5% pump speed, nitrogen and phosphorous (at a 9:1 ratio on a mM basis) are frequently supplied (every 4 to 2 hours) at 10% pump speed throughout the fermentation to keep nitrogen and phosphorous levels near starting concentration of fermentor heterotrophic growth media. The rest of the nutrients from the medium (except yeast extract) are supplied once every 24 hours of fermentation using a peristaltic pump at 10% speed. Dissolved oxygen is maintained above 30% by increasing the amount of sparged air into the vessel up to 4 L/min and agitation up to 300 rpm. Cells from the 10 L volume of non-triggered cells can be used to directly seed a 90 L volume (10 L culture+80 L fermentor heterotrophic media in an Eppendorf BioFlo 610 fermentor). The 90 L culture is fed as described with sparged air at 50-100 LPM and pitched blade agitation to 350 rpm. By this method the resulting biomass (6 g/L from an initial 0.2 g/L) is produced over 120 hours that includes no lag phase and a 96-hour extended logarithmic phase of high specific growth of 0.7/day. The use of these components is advantaged over current practices by the physiology of rapidly growing cells; culture pH shifts from nitrogen metabolism are managed by addition of organic acid, doubling as the carbon source, to balance the culture pH without adding extra salt to the medium. Samples (10 mL) are collected every 24 hours for dry weight analysis to determine specific growth rate and pigment content of algal product (FIG. 1, embodiment 40). 10 mL samples are immediately centrifuged at 3000 g for 5 minutes, supernatant is removed, cell pellet is frozen at −80° C. and freeze dried to determine dry weight. Pigments are extracted from ground freeze-dried biomass with 50 uL of acetone per mg of biomass for 5 minutes at room temperature. Absorbance of the cleared extract is read at 476 nm using a spectrophotometer (BioRad Smart Spec). Total pigments (mg) are calculated using the following formula $[A_{476}/217] \times [\text{Extraction Volume (mL)}] \times [\text{Dilution Factor}]$; where 217 is the extinction coefficient of astaxanthin in acetone. Percent pigment is calculated from the mg of pigments per mg of biomass equivalents in the extraction. At 96 hours biomass reaches 2.1 g/L with a pigment content of 1.5% in red macrozooids (FIG. 2—Right top); on a volumetric basis that is equal to 31.5 mg/L. This corresponds to a significantly higher rate of product formation (qp) of 0.33 mg/L-hour; compared to 0.063 mg/L-hour in Hata et al. (2001). This corresponds to a specific growth rate of 0.68/day (0.028/hour) over 72 hours with no detectable lag phase at 24 hours; compared to 0.21/day (0.009/hour) in Hata et al. (2001). The significant improvements for a heterotrophic production system of high specific growth rate notably due to cell division rather than cell enlargement, and over extended duration, are shown in FIG. 4. Cell lines with a similar specific growth rate and higher intrinsic pigment content produce higher qp values by the method of the invention, such that pigment content of 2.3% yields a rate of 0.5 mg/L-hr. Productivity can be further increased through cell type selection or adaptation, co-cultivation, fermentor seeding and operation, and other means such as exemplified.

The cells redden as ammonium concentration increases (2.5 mM and above) even when urea and phosphate are in excess and the fixed carbon source is non-limiting. It is understood that the process can be optimized for each cell type to select a preferred duration of the production cycle while achieving product formation, as it is ongoing during several days (for example see FIG. 2—left for astaxanthin product formation data). The method also applies to cell types that may have somewhat higher salt tolerance such as cells of *H. pluvialis* strain BM1 (Chekanov et al. 2014) to achieve growth well above the reported 0.095/day under photosynthesis and formation of astaxanthin without cell differentiation in the dark. For such cell types, urea and nitrate can both be used. Other ways for reddening include, but are not limited to, elevated temperature through fermentor programming and are known in the art. Eventually this will cause cell differentiation, which may be desired for some applications. For example, cysts settle easily compared to vegetative cells and may be preferred for dewatering. Included herein are other conditions that over extended periods result in encystment, and are acceptable for certain production schedules. The desired quality acceptable for industrial application of the pigment produced heterotrophically by the method of the instant invention is verified by HPLC to be equivalent chemically to photosynthetically produced product.

By virtue of the microalgal cultures being produced in closed culture systems to exclude contamination and to attain high densities in short periods of time while in the vegetative state, these algae cultures can serve to efficiently seed photobioreactors or raceways, lighted by solar radiation or artificial illumination, as part of a seed train or production cycle. A 200 L fermentor at 10 g/L cell density grown by the method of the instant invention can supply a 10,000 raceway at 0.2 g/L cells. According to the methods of the instant invention many permutations are possible. Thus products produced by methods of the instant invention are high density biomass that is then used in conventional microalgae production systems. The methods of the instant invention can also reduce the areal footprint and eliminates common contaminants and predators experienced in conventional production.

Example 4—Improved Heterotrophic Media Composition and Biomass Production by *Chlamydomonas* Cells Six 1 L cultures in 2 L flasks were grown as described in Example 3 in flask heterotrophic media. The cultures were concentrated and combined as in Example 3 into 3 L of fermentor heterotrophic growth media (same as flask heterotrophic media but supplied with only 0.25 g/L sodium acetate initially) in a 14 L fermentation vessel (Eppendorf-New Brunswick BioFlo 3000) with an initial biomass density of 0.05 g/L. The 3 L fermentation culture is incubated at 28° C. with gas exchange provided by 5 L/min sparged air and a pitched blade impeller at 100 to 250 rpm at pH 7.8. Fermentation culture is maintained and supplied with nutrients and organic acid as fixed carbon source as in Example 3 in a fed batch manner. Samples (10 mL) are collected every 24 hours to generate a growth curve and measure urea, phosphate, and ammonium levels in the nutrient media using methods well known in the art. Using *C. reinhardtii* KAS1001, a specific growth rate of 1.7/day (0.07/hour) over 72 hours is achieved reaching 8.25 g/L biomass; this is a significantly higher yield and extended accelerated growth with an almost doubled fermentation duration compared to previous best rate of 1.7/d (0.07/hour) for only 40-hours duration with biomass yield reaching only about 1.4 g/L (Zhang et al. 1999) before cessation of growth. The about 1.4 g/L biomass requires at least 2.8 g/L sodium-acetate or 34 mM which leads to growth inhibition with salt toxicity, and thus only a short duration at the specific growth rate and low cell densities. *Chlamydomonas* culture transferred into a 100 L bioreactor as described in Example 3 sustains a specific growth rate of at least 1.0/day over four days (production cycle: 120 hours). The initial cell density of 0.2 g/L generates final cell densities exceeding 20-30 g/L when grown under the conditions described for *H. pluvialis* in Example 3 with added 5 psi vessel pressure to increase dissolved oxygen as needed, demonstrating an extended period of high rate active cell division with no inhibition of growth. A similar process is applied to *Chlamydocapsa* and *Chloromonas* with adjustments to temperature and medium components as is known in the art.

Example 5—Ammonium Control in a Co-Culture of *H. pluvialis* Using *Scenedesmus obliquus*

A volume of 2.5 L of *H. pluvialis* KAS1601 was grown in heterotrophic flask medium as in Example 3. One liter of *S. obliquus* KAS1003 was grown in heterotrophic flask medium as described in Example 3 with a non-organic acid carbon source (3.6 g/L glucose) and an alternate nitrogen source (0.09 g/L ammonium chloride). The cultures were centrifuged as described in Example 3 and concentrated into a 3 L volume co-culture of *H. pluvialis* and *S. obliquus* in heterotrophic fermentation medium as described in Example 3 supplemented with 3.6 g/L glucose. Alternatively, the *S. obliquus* was embedded in alginate or porous beads as is known in the art, enabling endpoint removal using filtration, magnetics, or other means. The 3 L fermentation culture was maintained as described in Example 3. Samples were taken at 24-hour intervals to obtain biomass dry weight and to measure ammonium concentration. At 96 hours the ammonium concentration reaches only 1.4 mM ammonium whereas 45 mM ammonium is observed in the 3 L fermentation culture of *H. pluvialis* from Example 3. This 3 L fermentation gives a specific growth rate of 0.77/day (0.032/hour). The final biomass is comprised of about 99% or more of *H. pluvialis* biomass, similar or superior to what may occur naturally in an open pond with mixed microorganisms. Adjustment of co-cultivation parameters such as dosing of the cell types or the glucose as a fixed carbon source allows reaching different target rates of growth and productivity relative to the carotenogenesis trigger of about 2.5 mM ammonium. A fermentation culture started with 0.2 g/L of biomass of *H. pluvialis* with appropriate ammonium control experiences an extended logarithmic phase of at least 96 hours with a specific growth rate of 0.77/day and a yield of 4.3 g/L biomass in 120 hours. A fermentation culture started with 1 g/L of biomass of *H. pluvialis* with appropriate ammonium control has a 96-hour extended logarithmic phase with a specific growth rate of 0.77/day and yield of 22 g/L biomass in 120 hours. The last 48 hours are with ammonium stress, the first 24 (hour 72 to 96) of which biomass is still accumulated at the same specific growth rate as log phase and the second 24 (hour 96 to 120) of which astaxanthin is accumulated to 1.5% of the dry weight of motile cells. This 120-hour fermentation run yielded a far superior qp of pigments at 5.5 mg/L-hour compared to Hata et al. (2001), which showed significantly lower yield of 0.063 mg/L-hour. Unlike the prior art, where high growth rates are sustained for only short periods as biomass accumulates and also cell division ceases during pigment production, the method of this invention allows extended high specific growth rates over many days, including beyond 7 days if desired. In this example, it is understood that the *S. obliquus* can be interchanged with a different microbial cell type suited to heterotrophic growth as long as it still prefers a fixed carbon source that is not an organic acid and preferentially consumes ammonium as nitrogen source, as is known in the art for many such cell types. Options among astaxanthin or other pigment producing cell types or for oil-producing cell types are other species of *Scenedesmus, Chlorella, Monoraphidium, Rhodotorula* (a red yeast), and many different diatoms such as *Phaeodactylum* and *Cyclotella*, and thraustochytrids or thraustochytrid-like cell types, as known in the art. Biomass from the co-cultures can contribute products of value from one organism to complement that of the second organism, especially when the ratio of cells is manipulated favorably. For example, diatoms contain fucoxanthin, *Scenedesmus obliquus* contains water-soluble carotenoprotein, thraustochytrids contain DHA fatty acids.

Example 6—Ammonium Control in a Co-Culture of *H. pluvialis* Using *Chlamydomonas reinhardtii*; and Conditions Favorable to Carotenogenesis Three liters of *H. pluvialis* KAS1601 were grown in heterotrophic flask media as in Example 3. One liter of *C. reinhardtii* KAS1001 was grown in heterotrophic flask media as described in example 3. The cultures were mixed in to a co-culture of *H. pluvialis* and *C. reinhardtii* in heterotrophic flask media as described in Example 3, with between 5 mM and 20 mM Na-acetate. The 3 L fermentation culture was maintained as described in Example 3. Samples were taken at 24-hour intervals to obtain biomass dry weight and to measure ammonium concentration. Ammonium concentration as effectively maintained below 1 mM for the 120-hour fermentation, whereas the monoculture of *H. pluvialis* in Example 1 reaches 45 mM ammonium. This 3 L fermentation gave a specific growth rate of 0.90/d (0.038/hr) over 96 hours. The final biomass was comprised of about 99% *H. pluvialis* biomass, similar to what may occur naturally in an open pond with mixed microorganisms. Adjustment of co-cultivation parameters such as dosing of the cell types or operational parameters such as rpm and oxygenation, typical of fermentation systems allows reaching different target rates of growth and productivity relative to the carotenogenesis trigger for *H. pluvialis* of about 2.5 mM ammonium. We observed the microalgal culture to produce astaxanthin at a specific productivity rate far exceeding the previous reported values of 0.063 mg/L-hour, namely we obtained 1.0 mg/L-hour, and preferably higher at 1.875 mg/L-hour with 15 g/L biomass at 1.5% astaxanthin, and even higher at 3.75 mg/L-hour with 15 g/L biomass at 3% astaxanthin at 5 days; notably this being 30- to 60-times higher than 0.063 mg/L-hour in heterotrophic growth (from Hata 2001).

Additional intrinsic or extrinsic triggers are effective in product formation throughout the vegetative growth of the culture and in complete darkness. For isoprenoid production these can be termed "conditions favorable to carotenogenesis", and are described for example in FIG. 3 and Example 9. It is understood that while examples are providing for ammonium accumulation as a favorable condition, other conditions favorable to carotogenesis can be substituted wherever ammonium is referenced. These conditions favorable to carotenogenesis include ammonium in excess (>2.5 mM), phosphate deplete, sulfate deplete, urea deplete, NaCl or other osmotic contributor greater than 2.6 g/L, lactic acid in excess of 3 g/L, an increase in temperature 2 degrees Celsius above the growth temperature, or any combination or substitution thereof. Conditions may include additional supply of precursor compounds affecting carbon flux notably in the isoprenoid pathway. Using the method of claim 1, as exemplified but not limited to Examples 5 and 6, under these favorable conditions cell division does not cease, cells remain the same size or even slightly smaller than green macrozooids of 10-12 microns in length (excluding the flagella), are motile and retain their flagella, and organic acid supply is non-limiting.

Example 7—Heterotrophic Cell with Altered Isoprenoid Production in Mutants or Genetically Engineered Organisms This example pertains to a heterotrophic cell with altered expression for phytoene, geranylgeranyl pyrophospate, phytofluene, and other upstream accumulating pigments or pigment precursors as well as other sinks such as terpenes. Such a cell grown heterotrophically can be used in the method of the present invention. For example, phytoene (colorless) and phytofluene (pigmented) have exceptional value in UV absorption in cosmetics. A heterotrophic cell with high pigment accumulation makes an ideal starting material for treatment through mutagenesis or genetic engineering to create a high phytoene (or other compound) cell and cell lines by halting or slowing flux to the original endpoint pigment. A 5 mL heterotrophic vegetative culture of *H. pluvialis* in heterotrophic flask media as in Example 3 was mutagenized when it reaches an OD750 of 0.15 using a CL-1000 UV Crosslinker (254 nm UV-C light) for 1 minute at 13 cm from light source such that 50% cell death occurs. After 120 hours of recovery at room temperature in the dark without shaking sufficient ammonia built up in the media such that carotenogenesis began. 5 mL of cells were centrifuged and 4 mL of media was removed. DAPI (4',6-diamidino-2-phenylindole) is added (1 µg/mL) immediately before filtering cells through a 50 µm membrane before flow sorting. Cells that did not produce astaxanthin or other colored pigments were isolated using flow cytometry. Isolation and selection was performed based on differential fluorescence, being high at 530 nm with low autofluorescence at 695 nm when using a 488 nm light source. The isolates were grown up to 5 mL volumes as in Example 3 flask heterotrophic media for 120 hours for phytoene content quantification. Phytoene was extracted from freeze-dried and ground biomass using 1 mL of acetone per mg of biomass. Phytoene content analysis from the same mutant isolate is performed for a different vegetative grow out and carotenogenesis cyst formation cycle to ensure reproducibility. In the process of isolating phytoene-accumulating mutants, a cell that differentially accumulates compounds other than astaxanthin (as in the normal wild type) accumulated lutein, lycopene, beta-carotene, canthanxanthin, or phytofluene or even associated geranylgeranyl pyrophosphate as can be identified based on a new and different autofluorescence signature. This heterotrophic cell, by virtue of being cultivated in the dark while supplied with exogenous organic acids, expresses the alternate phenotypes with no detrimental growth effects. This is notably beneficial for phytoene mutants. This example also applies to the use of an achlorophyllic phenotype with the changes in lutein signature. The pigments were confirmed by HPLC as is known in the art. Biomass from this heterotrophic cell can be targeted for introduction of exogenous enzymes such as phosphatases, or for isolation of the accumulated precursor for use in chemical modification. This cell can originate from mutagenized or genetically engineered material that affects enzymes in the biosynthetic pathway such as phytoene desaturase knock out or knock down or lycopene cyclase and downstream knock out or knock down.

Similarly, a heterotrophic recombinant cell with added isoprenoid or terpene synthase, such as for pinene and limonene, with isoprenoid synthases being numerous and well known in the art and capable of being optimized, or modified geranylgeranyl pyrophosphate or other precursor molecules as known in the art, can first be indirectly selected using the FCM-based steps described above, as shunting into these molecules can cause a detectable decrease in the original sink carotenoids (Wang et al. 2015) to yield lower autofluorescence at 530 nm compared to wild type or original untreated control. Many terpenes serve a function in consumer goods, but also for bioenergy as in limonene as a fuel additive. A nuclear heterotrophic *Chlamydomonas* cell recombinant for limonene synthase expression was generated, using a vector modified using methods understood by those in the field, for insertion into the rDNA IGS following US patent application publication no. 20090317878 or for use with the GeneArt® *Chlamydomonas* Engineering Kit (Thermo Fisher Scientific), comprising limonene synthase, plastid targeting and expression elements (Syrenne and Yuan, 2014). Notably limonene is volatilized from the microalgae into the headspace above a liquid culture for subsequent separation. Alternatively a plastidic heterotrophic *Chlamydomonas* cell recombinant for limonene expression was generated by insertion via homologous recombination of limonene synthase from *Mentha spicata*, using methods known in the art or that described in Example 12 for recombinant *Chlamydomonas* chloroplast. Similarly a nuclear or plastidic heterotrophic *Haematococcus* cell recombinant for limonene expression was generated using the methods of Alonso-Gutierrez et al. 2013 (for the plastid), or Sharon-Gojman 2015 (for nuclear and plastid), and selected using FCM selection as described in the above examples. They were then subjected to fermentation culture to achieve a specific growth rate in excess of 0.7 per day for 72 hours following the examples above.

Example 8—Isolating an Ammonium-Tolerant or Carotenogenesis-Triggered Heterotrophic Cell with Fast Accumulation of Pigments Any carotenogensis trigger or combination of triggers can be used to generate the cells for flow sorting. As an example using excess ammonium, a 5 mL vegetative culture of *H. pluvialis* in heterotrophic flask media as in Example 3 was induced to form carotenoids by allowing ammonium in the growth medium to build up to 2.5 mM or higher for example. Motile cells with elevated carotenoid (reduced chlorophyll) content are isolated via flow cytometry using a FACS Aria flow sorter after 8 to 48 hours of ammonium stress. To ensure isolation of motile cells DAPI was added to the sorting media to identify motile cells (DAPI positive) and cysts (DAPI negative); the DAPI positive cells with low autofluorescence from 695 nm have low levels of chlorophyll and the DAPI positive cells with high autofluorescence from 530 nm have elevated beta-carotene (a proxy for eventual astaxanthin accumulation). Using methods as described in Example 1, from 96-well plates the single cells isolates were grown up to 5 mL volumes as in Example 3 and transferred to carotenogenic formation conditions for astaxanthin content quantification. Astaxanthin is extracted from freeze-dried and ground biomass using 1 mL of acetone per mg of biomass. Astaxanthin content analysis from the same isolate is performed for a different vegetative grow out and carotenogenesis cycle to ensure reproducibility. Extending the time period of ammonium stress beyond 48 hours specifically selects for one or more cells that do not readily differentiate and encyst, to accumulate carotenoids to generate subpopulations that will remain motile as macrozooids even after extended stress conditions. A cell selected by this method can have any number of pigment traits, including being colorless or exhibiting accumulated precursors or other isoprenoids, and is not limited to astaxanthin.

A fast pigment accumulation phenotype for a cell selected under specific conditions for carotenogenesis appear highly heritable or unique to those specific conditions. In other words, the genotype×environment response appears strong, such that a sulfate-deplete responsive cell with a 10% increase in astaxanthin content over the original population may not show the same response under urea depletion as a different condition for carotenogenesis trigger is used. As an example how to isolate a carotenoid rich heterotrophic cell with fast accumulation of pigments after sulfate depletion as the condition favorable for carotenogenesis, a 5 mL vegetative culture of *H. pluvialis* in heterotrophic flask media as in Example 3 is induced to form carotenoids by transferring cells to growth medium lacking sulfate. Motile cells with elevated carotenoid (reduced chlorophyll) content are sorted and isolated via flow cytometry 8 to 48 hours after the carotenogenesis trigger. Cells are grown as unique lines. The carotenoid profile is analyzed via HPLC to determine proportions of pigments present (FIG. 3), each trigger and combination of triggers can yield different carotenoid profiles.

Example 9—Use of Algal Product

There are many different ways to utilize the intact biomass or extracted components in numerous feed, food, nutraceutical, pharmaceutical, cosmetic, and crop protection applications, as well as many other applications. Some non-limiting examples are provided here, using carotenoids as a desired component. For example, astaxanthin-containing product obtained by the method of this invention is either extracted, or retained in whole biomass, or is a residual in processed biomass such as delipidated meal, to be used for animal feed, human nutrition and nutritional supplements, personal care and cosmetics, and as colorant. The general composition of *Haematococcus* algal biomass or meal consists of common carotenoids, fatty acids, proteins, carbohydrates, and minerals. The astaxanthin in *Haematococcus* is approximately 70% monoesters (linked to 16:0, 18:1 and 18:2 fatty acids), 25% diesters and 5% free pigment. This esterified composition is similar to that of crustaceans, the natural dietary source of salmonids, and is readily metabolized. At 1.5% astaxanthin content, about 5.33 kg of *Haematococcus* algae biomass or meal is added per ton of feed to achieve an astaxanthin concentration of 80 ppm typical of this colorant approved for feed. The protein and other fractions of the intact biomass provide additional feed value, notably not provided by artificial astaxanthin (that is chemically synthesized and unsustainable). The relative fragility of the thin-walled whole algae produced by method of this invention is advantaged over the alternative of thick-walled aplanospores for ease of cell disruption, with associated benefits for digestibility and nutrient availability to impact fish fingerling health and growth that can be quantified as is known in the art.

Pigment extract from the method of this invention is handled, processed and used similar to the pigment extract from phototrophically produced material as is practiced in the industry. For example, ethanolic extractions, supercritical fluid extractions, and pressurized liquid extractions are acceptable practices in the personal care and cosmetics ingredients industry. Whereas an extract from *Haematococcus* biomass that is grown photosynthetically and induced to accumulate carotenoids in the light is well known to consist predominantly only of astaxanthin (about 85% up to 99% of the total carotenoids), an extract of heterotrophically grown pigmented biomass from *Haematococcus* using the method of the instant invention yields not only a predominant astaxanthin profile but can also yields a unique mixtures of various natural and useful pigments with personal care properties. Several such novel mixtures are shown in FIG. 3 and are non-limiting. Heterotrophic sulfate depletion (FIG. 3A)—which can occur intrinsically by calculated depletion kinetics due to cell growth and nutrient consumption during the course of the production run—for example results in a unique lutein-rich and astaxanthin-rich carotenoid composition wherein the lutein can comprise half the amount as astaxanthin; and lutein with carotene comprises over one-third (37%) the total carotenoids; and the astaxanthin comprises over half (57%). This is useful for filtration by the lutein of blue light (including high energy visible blue light from solar radiation or artificial light from screens of electronic devices) and further protection from UV damage, oxidative stresses and inflammation by the astaxanthin. This novel extract serves to deliver, in combination, compounds that are currently consumed or applied individually to benefit eye retinal health and to even skin coloration. This natural fusion of bioactive compounds can further include pigments present in a second cell type, for example a diatom, which naturally contains fucoxanthin and diadinoxanthin for additional blue light protection at somewhat different wavelengths (about 420 to 520 nm for lutein, 380 to 480 nm for fucoxanthin). Canthaxanthin (up to 5%) can also comprise the pigment mixture (FIG. 3), a carotenoid recognized to be of value in skin care as well as feed applications.

The malleable pigment profile of the heterotrophic cells, wherein they are not differentiated into aplanospore cysts, can be modified or customized for other uses of the algal product by employing calculated kinetics for urea depletion (FIG. 3B) or ammonium accumulation of similar pigment profile, phosphate depletion, or extrinsically applied osmotic stress (FIG. 3C). Unusually, the extracted resin can be remarkably oily, such as per urea stress, or relatively not oily, such as per sulfate stress, and possess phytosterols. By way of example, the oleoresin produced by extraction of microalgal biomass contains fatty acids comprised of C16:0 (29%), C18:1ω9 (20%), C18:1ω7 (3.5%; with Omega-7 fatty acids purported to support skin health), C18:2ω6 (21%; with linoleic reported to induce beneficial skin cell autophagy), C18:3ω3 (7%), and C20:4ω6+C20:5ω3 (1.5%).

One example of a cosmetic raw ingredient produced by the method of the instant invention is AstaFusion (CAS Registration Number 1174756-78-5) with an INCI designation as *Haematococcus* Pluvialis Extract. The extracted resin combines astaxanthin with carotene, lutein/zeaxanthin, and canthaxanthin with minor carotenoids in a natural amber to orange blend not found in current algal astaxanthin raw material in the market.

The fusion of pigments can work in synergy for numerous broader personal care health effects. For example, as a blue-light filter in a topical skin care product, the AstaFusion resin extracted by ethanol from biomass is prepared on a lutein+carotene (or just lutein) basis dispersed in butylene glycol, squalane, or oil for final inclusion rate of 0.005 to 0.05%. The resin easily solubilizes to produce, for example, 50-60% algal oleoresin in 40% squalane by volume, or 30% algal oleoresin into 70% botanical oil, preserved with 1% alpha-tocopherol. For performance data, photoprotective activity values can be determined by measuring the skin surface redness with a Minolta Chroma Meter as is known in the art. In broad-acting skin serums, creams and oils, inclusion rate can be calculated on an astaxanthin basis ranging from about 1.5-3 ug/ml astaxanthin (5-10 uM) minimum, more preferably 6 ug/ml, and even more preferably about 30 ug/ml (about 50 uM) to attain genetic, biochemical and physiological, and in vivo effects. For example, AstaFusion demonstrated potential for collagenase inhibition of about 35% from a dried ethanol extract from *Haematococcus pluvialis* KAS1601 containing 4.8 ug astaxanthin per 1.0 mL of reaction.

As another example, based on a preliminary transcriptome-wide microarray study using Illumina HT-12 gene chips to identify differentially expressed genes in a normal human fibroblast cell line as is known in the art, targets for further study after treatment with AstaFusion can include reducing expression of skin matrix-degrading gelatinases (MMP-2 and MMP-9) through the activity of the TFPI2 gene; activating the major control point transcription factor p53/TP53 via elevated expression of E2F7 and IRF1; and potential for improved protection of cells from oxidative stress through decreased gene expression of TXNIP.

Other effects can be measured as is known in the art, including, but not limited to skin elasticity, skin hydration, surface skin lipid levels, skin lipid peroxidation, wrinkle appearance, and can be measured in laboratory tests including, but not limited to, free radical quenching, antioxidant capacity, autophagy, DNA protection, telomere support, and anti-inflammatory effects and cytokine regulation measuring factors including, but not limited to, production of NO, TNF-α and PGE2, COX2, etc.

As an orally ingested nutrient supplement, astaxanthin and the other antioxidant and anti-inflammatory pigments are known for skin support, as well as joint health, UV protection, sports performance recovery, robust immune function, anti-aging, increased energy, cognitive health and nootropic, and cardiovascular support. AstaFusion resin extracted by supercritical fluid from milled biomass is prepared on an astaxanthin basis dispersed in an edible oil of safflower. Alternatively, the raw ingredient is formulated in beadlets and powders as is known in the art. They are used for fortifying and coloring foods and supplements that may be in forms such as margarine, edible oils, and snacks, beverages, soups, sauces and dressings, cereals and confectionery; up to 80 uM in oral dosage is known to have beneficial effects on facial wrinkles. Demonstrated human nutrient supplements can serve as a gateway to pet food inclusion or pet treats. As another example for use as a cosmetics raw ingredient; heterotrophically grown pigmented whole biomass of *Chlamydocapsa* was lysed in the presence of liposomes or phospholipid carriers, or treated with maltodextrose, to produce a bioactive material for skin care formulations.

Example 10. Transgenic Heterotrophic Pigmented Cell from *Chlamydomonas, Chlamydocapsa*, and *Chloromonas*

This example is directed towards a cell from *Chlamydomonas, Chlamydocapsa*, or *Chloromonas* producing pigments without cell differentiation and at desired growth rates. In one manifestation using *C. reinhardtii*, beta-carotene ketolase and carotenoid hydroxylase from *H. pluvialis* are cloned into a plasmid containing promoters for $CO_2$ induced expression, such as described in US patent application publication no. 20090317878, and optional endogenous control elements from *H. pluvialis* or *C. reinhardtii*, as known in the art. Further, use of IPP isomerase and the mevalonate pathway elevates isoprenoid production, for example, as described in U.S. Pat. No. 7,129,392. The plasmid was transformed into the nucleus of *C. reinhardtii* and transgenic lines were selected as known in the art. Transgenic lines were screened for pigment content and heterotrophic growth as described in Example 8 and Example 4, respectively. A biohydrogen co-product is generated during the last few hours of fermentation using the methods as described in Example 11. In another manifestation, the cell of *Chlamydomonas, Chlamydocapsa*, or *Chloromonas*, which normally accumulates elevated pigment by undergoing cell differentiation after exposure to nutrient deprivation and high light (the two stage process of the Chlamydomonadales), was cultivated as described in Example 3 to yield a pigmented vegetative cell in the absence of light, nutrient deprivation and cell differentiation.

Example 11. Transgenic Heterotrophic Cell of *H. pluvialis* Modified to Produce Biohydrogen Product This example describes biogas as a stand-alone product or as a co-product with pigment or other accumulating compound. Hydrogenase A1 and A2 (HYDA1 and HYDA2) from *C. reinhardtii* along with auxiliary proteins HYDE, HYDF (fused in *C. reinhardtii* as HYDEF), and HYDG were cloned along with their respective endogenous control elements (or optional ammonium induced promoters) into a plasmid as known in the art. The plasmid is transformed into the nucleus of *H. pluvialis* as is known in the art (Sharon-Gojman et al. 2015). Transgenic lines were screened for pigment content and heterotrophic growth to select a preferred strain such as in Example 8. The co-product (biohydrogen) and mRNA levels of transgenes were screened under anoxic conditions (anaerobic fermentation) after sufficient pigmented biomass with high levels of internal starch have been generated under aerobic conditions. The duration of $H_2$ evolution is proportional to the amount of stored carbohydrate in the cell as starch catabolism provides the electrons to the hydrogenases under dark fermentation conditions. This is a particularly advantageous process, as the pigment or astaxanthin accumulates in cells stressed by fermentation at very low dissolved oxygen (along with stress from ethanol, lactate, or formate that forms). This way the last few hours of the fermentation can be used to produce two products (one high value and one low value), if desired. Advantageously, with extraction, this biomass appears to have higher pigment content as internally stored starch (weight) has been converted into extracellular products. Wild type or genetically modified *Chlamydomonas* species can also be used for biogas, as is known in the art. The method of the invention enables higher biomass density in a short time period not possible previously due to salt inhibition for these Chlamydomonadales, with higher biomass yielding higher biogas productivity on a volumetric basis. A productivity rate of about 0.96 mmol $H_2$/g dry weight-hour under anaerobic conditions from 4.3 g/L biomass culture evolves hydrogen on a volumetric basis up to 4.13 mmol hour, a significant improvement, for example, from the 0.13 mmol $H_2$/L-hour in *C. reinhardtii* as shown by Yu and Takahashi 2007, with a calculated low cell density of 0.135 g/L.

EXAMPLE 12. HETEROTROPHIC CELL MODIFIED TO PRODUCE A RECOMBINANT PRODUCT OF INTEREST

Figure 5:
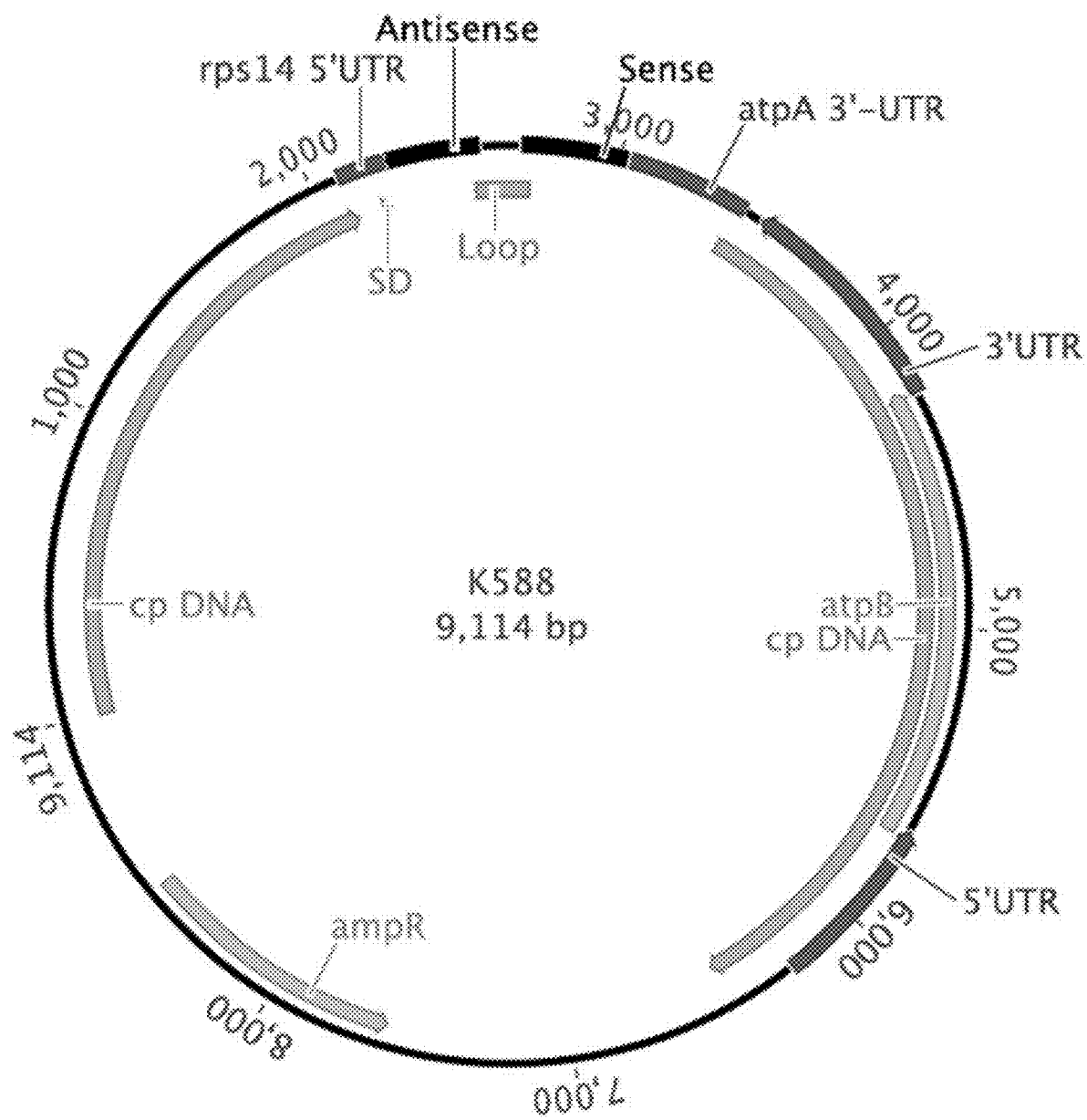
FIG. 5. Example of a plasmid vector, K588, used in the instant invention for double-stranded RNA expression in *Chlamydomonas reinhardtii* KAS1402 suited to high-rate heterotrophic growth.

This example is directed to a heterotrophic cell that is cultivated with a preferred growth rates and specific productivity to produce a recombinant product using fed-batch fermentation using the method of the invention. In addition to the molecules already exemplified (such as pigment, terpene, biohydrogen) a recombinant cell useful for the present invention produces a heterologous RNA (including dsRNA) or heterologous protein of interest. Such a recombinant cell was genetically engineered as known in the art and with application in numerous fields including, but not limited to, oral therapy, crop protection, disease protection and health promotion in aquaculture and animal husbandry, flavor and fragrance (Somchai et al. 2016; Cerutti et al 2011; Machado et al. 2014; Kumar et al 2013; Gimpel et al. 2015). Manifestations were given here for plastidic thaumatin gene expression (thaumatin is a protein used for flavoring and flavor masking) and for dsRNA expression in *C. reinhardtii*. Plastid expression is well known to express complex proteins and also dsRNA as the plastid lacks RNAi processing of the DICER/RISC complex. An atpB deficient mutant of *C reinhardtii* KAS1402 is transformed via bombardment (1100 psi, 6 cm target distance) with 0.6-micron gold particles coated with vector K497 containing atpB and control elements along with chloroplast codon-optimized thaumatin controlled by the rps14 promoter. Transgenic lines are selected photosynthetically on medium lacking a fixed carbon source. After three rounds of single colony selection and isolations on medium lacking acetate (photosynthetic) the transgenic lines were moved to heterotrophic growth conditions as in Example 3. Expression analysis proceeds by qRT-PCR, using primers 585: CTGCTATTTCGACGACAGTG and 586: ACGAGAACTCCGCTAAAGTG, following manufacturer's instructions (iScript™ One-Step RT-PCR Kit With SYBR® Green 170-8892). The thaumatin mRNA levels in transgenic lines were similar to that of a chloroplast housekeeping gene, Rp114, levels while no expression was seen in the wild type. Recombinant protein at 0.1% harvested at 120 hours with 10 g/L cell density produces a qp of 0.08 mg/L-hour, at higher harvest density this will exceed0.08 mg/L-hour. For dsRNA expression in *C. reinhardtii* KAS1402, thaumatin is replaced in the expression vector with a 789 bp sequence inverted repeat construct for a 3-I IKT gene fragment (adapted from Kumar et al. 2013) synthesized by GenScript and shown in vector K588 (FIG. 5). The annotations of vector K588 are shown in Table 1.

TABLE 1

| Type | Name | Minimum | Maximum | Length | Direction |
|---|---|---|---|---|---|
| misc_feature | Cp DNA | 1 | 2100 | 2100 | forward |
| 5'UTR | rps14 5'UTR | 2106 | 2229 | 124 | forward |
| misc_featare | SD | 2218 | 2221 | 4 | forward |
| 3-HKT RNA | Antisense | 2234 | 2535 | 302 | none |
| misc_feature | Loop | 2542 | 2702 | 161 | none |
| 3-HKT RNA | Sense | 2703 | 3004 | 302 | none |
| 3'UTR | atpA 3'-UTR | 3012 | 3417 | 406 | forward |
| misc_feature | Cp DNA | 3418 | 6455 | 3038 | forward |
| 3'UTR | 3'UTR | 3507 | 4214 | 708 | reverse |
| Gene | atpB | 4213 | 5689 | 1477 | reverse |
| 5'UTR | 5'UTR | 5690 | 6227 | 538 | reverse |
| Gene | ampR | 7630 | 8490 | 861 | reverse |

An alternative vector configuration is possible for the dsRNA to be generated post-transcription by using opposing promoters, as is known in the art. Selected colonies are grown heterotrophically according to Examples 3 and 4. Verification of an initial specific growth rate over 0.7 per day for 72 hours shows suitability for scaling towards industrial manufacture. A culture is scaled using fed-batch fermentation to 50 L in a 100 L reactor (Eppendorf BioF1o610) according to Examples 3 and 4 for a sustained specific growth rate of 1.0/day over four days. Biomass is dewatered using a continuous centrifuge (WVO Designs Power Beast 3500 rpm centrifuge) and freeze-dried (12L Console 230-60 FreeZone LabConco lyophilizer assembly) for analytical purposes and to establish kinetics.

At the smaller scale, dsRNA expression and accumulation is tested by gel electrophoresis of total RNaseA treated RNA relative to standards. Densitometry is by Quantity One® software (Bio-Rad). Initial dsRNA values are considered successful if they exceed that reported in bacteria, namely 400 ng per 10^8 cells (Kim et al. 2015); or that reported for a transplastomic plant of 0.05% to 0.4% of total cellular RNA (Zhang et al. 2015) at 120 hours or longer.

Recombinant RNA at 0.05% from cell mass at 10 g/L at 120 hours produces a qp of 0.04 mg/L-hour. The qp is expected to increase by at least 15% over baseline through improvements of culture conditions, for example, including operations at higher starting cell density with higher inoculum greater than 0.2 g/L, higher specific growth rate such as 1.7/day or higher, and longer cycle time extending beyond 120 hours.

A cell that is genetically modified using nuclear transgenesis and inducible promoters is also suited to be cultured heterotrophically by the method of the instant invention. For example, use of a nuclear vector comprising the intergenic sequence IGS spacer region of an rRNA locus plus promoters and adjoining sequences enables expression of inserted sequences. The nuclear inducible promoters AMT1;2 5'UTR (U.S. Pat. No. 9,487,790) provides a transgene expression system in algae that is responsive to low nitrate (<0.1 mM), high ammonium (7.5 mM) in the culture medium. Using the method of the instant invention, a Chlamydomonas cell and cell culture first grown heterotrophically in medium void of nitrate with urea maintained as in Example 3 for initial biomass accumulation undergoes induced gene expression if the last 36 hours of culture are provided with elevated ammonium (maintained at 7.5 mM). This is useful for a strategy to increase levels of dsRNA through added nuclear expression using inducible Dicer suppression or for other sequences suited to nuclear expression. Transgene transcription using an AMT1;2 ammonium transporter gene promoter is tightly repressed in the presence of ammonium or nitrate, and rapidly induced in its absence. An initial dsRNA value exceeds that reported in nuclear transgenic algae of 40 ng per 10^8 cells, measured as is known in the art (Somchai et al. 2016).

For scale-up purposes biomass pulverization- to facilitate bioavailability of internal payload—by any number of means can be used as part of downstream processing prior to application in the field; bead milling or dry pin milling of microalgae was effective in cracking cells. The half-life of dsRNA inside UV-exposed algae is unaffected by milling, as monitored for dsRNA integrity over time by agarose gel electrophoresis and stained band quantification by gel analysis software. However, cell disruption is not required for exposure of algal-encapsulated dsRNA for feeding larvae in water bodies or on plant parts, and wet biomass can also be utilized. Larval feeding on leaves show weight gain or mortality at 50% of water controls after 7 days; insect larval weight, instar stage, and mortality (immobility) are analyzed using leaf discs and whole plants as is known in the art (for example Zhang et al. 2015). A concentration-response on larval health is seen with algal dosage (measured as equivalent µg dsRNA per leaf or volume water), for intact and milled cells.

Being generally regarded as safe, the Chlamydomonas biomass can be titrated to deliver appropriate levels of thaumatin to promote palatability in animal feed, or to deliver other recombinant molecules that can be produced in the same manner such as for antibiotic replacement using milk proteins in poultry feed, or even as a dsRNA-based microalgal larvicide to control mosquitoes or other insects and nematodes.

Example 13: Heterotrophic Cultivation of Various Phenotypes

This example is directed to novel heterotrophic cell types that are cultivated with conditions favorable to vegetative growth and making product using the method of the invention. Using C. reinhardtii as an example, strain KAS1602 (a variant derived from CC-125 or 137c) was grown in heterotrophic flask medium as in Example 3. The cell type was characterized as non-flagellated, achlorophyllic, and of yellow color (in part from lutein/zeaxanthin) rather than green appearance as vegetative cell. It was derived from a population of previously cryopreserved cells revived under mixotrophic conditions for growing cells in a shake-flask with 30 µE light for one week, and then subcultured into conditions conducive to heterotrophic vegetative growth as in flask medium of Example 3 (as stationary flask in the dark) for 2 weeks, isolated from flagellated cells based on its inability to be phototaxic when a light source is provided at the top of a vessel. It retained its phenotype for numerous generations under heterotrophy with robust growth. The example also pertains to cell types of UV light-induced and chemically induced Chlamydomonas mutants that lack carotenoids or are flagellum-less, for example through phytoene synthase gene mutations such as mutant strain lts1-30 mt-(CC-2359) obtained from the Chlamydomonas Resource Center or generated as described in the art (for example McCarthy et al. 2004 for pigment mutants and McVittie 1972 for flagellum mutants), or that have other defects as photosynthetic or flagellum mutants. Further the example applies to algae that undergo genetic engineering to render them capable of growth in darkness. This can include without limitation obligate phototrophs that are genetically engineered into facultative heterotrophs, including for trophic conversion or for utilization of the preferred carbon feedstock as is known in the art. This also includes without limitation facultative heterotrophs that are rendered obligate heterotrophs or have weakened photosynthetic ability such as attained through variants, mutants, and genetic engineering. In fermentation the non-flagellated cell type is advantaged in that it is less prone to mechanical damage from the impeller (pitched blade or Rushton impeller), allowing fermentor operation at higher rpm than 350 rpm for improved gas exchange and nutrient mixing. In addition it benefits from a reduced metabolic burden from not producing unnecessary chlorophyll in the dark. The resulting biomass of KAS1602 and mutant strain lts1-30 mt-(CC-2359), lacking green or other pigments, is desirable for use in cosmetics, feed, and such.

Example 14—Mixotrophic Media Composition and Pigment Production by Macrozooid *H. pluvialis* Cells This example is a modification of Example 3, including the nutrient medium with organic acid and urea, such that heterotrophic growth was replaced by mixotrophic growth under 30 light. The specific growth rate of *H. pluvialis* KAS1601 reached 1.5/day such that a culture starting with 0.05 g/L biomass reached 9.0 g/L in 96 hours. The pigment content of the biomass reaches 2.3% corresponding to a qp of 2.2 mg/L/hr. Optionally the method of the invention can be practiced to obtain algal product with additional finishing steps as is known in the art (such as discussed in narrative). For example, added stress or light or an inducer can be supplied to elevate product yield or form cysts with elevated product content (see FIG. 2—Right bottom for astaxanthin-rich cysts).

Example 15—Pigmentation Supplement and Nutrient Supplement Compositions from Non-Encysted Microalgae The new process provides a substantially new profile of biomass from the Chlamydomonadales that is pigmented with high protein, low ash along with vitamins and minerals, yielding a new product composition that confers nutritional, health or coloration benefits. For feed additives such as for poultry and fish, these benefits are comparable to those provided by fish-derived ingredients while serving the purpose of providing pigmentation for coloration. For meal replacement beverages or nutritional supplements, the composition serves a nutrient additive purpose. Depending on the source microalgae, the composition as a food could be as a source of carotenoid in the diet, with any colorant properties considered incidental; or as in the case of beta-carotene, the material could be used as both a nutrient supplement and a color additive. Biomass grown as described above is harvested from the fermentor, lyophilized, and then analyzed for its major components according to methods of the Association of Official Analytical Chemists (AOAC) performed by New Jersey Feed Lab (Trenton N.J.) or similar. The non-encysted biomass is then processed into a form suitable for feed formulation and coloration or food addition as is known in the art. The protein content of pigmented vegetative cells is essentially doubled that of encysted cells or photoinduced cells, comprised of about 0.4 to 0.5 g/g DW protein, compared to 0.19 to 0.24 g/g DW protein in commercial pigmented whole biomass used in feed or foodstuffs such as for *Haematococcus* spp. or *Dunaliella* spp. (Lorenz 1999; GRAS Notice grn000356; GRAS Notice grn000276; Muhaemin and Kaswadji 2010). Ash is reduced by about 50-80%, from 0.16 to 0.18 g/g DW ash to about 0.03-0.09 g/g DW ash. The new composition with high protein along with low ash content thus has higher overall nutritional value on a weight basis; fish protein currently costs over $1500/ton and thus represents a substantial input cost for feed which can be preferably replaced by algal protein while delivering the coloration additive (i.e., colorant). It also differs favorably by having much lower fiber compared with defatted *Haematococcus* meal from encysted biomass (such as remaining after astaxanthin extraction): the defatted meal from encysted biomass approaches a similar protein content with 0.4 g/g DW protein but it also carries along an undesirably high amount of 0.4 g/g DW fiber. Astaxanthin comprises up to 80 mg per kg salmon feed (Wrolstad and Culver 2012) while protein-rich fishmeal can comprise 200 g per kg feed (Hatlen et al. 2013). At 80 mg astaxanthin per kg feed, 11.4 g algae/kg feed is required with 0.7% pigment content; and it provides a 3% fishmeal replacement rate, with 50% of the algal biomass as protein, that can be monetized.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Journal Articles

1. Aflalo C, Meshulam Y, Zark A, and Boussiba S. 2007. On the relative efficiency of two-vs. one-stage production of astaxanthin by the green alga *Haematococcus pluvialis*. Biotechnol. Bioeng. 98:300-305.
2. Alabi A O, M Tampier, E Bibeau. 2009. Microalgae technologies and Processes for biofuels/bioenergy production in British Columbia: Current technology, suitability and barriers to implementation. Seed Science Ltd pp 30-38.
3. Alonso-Gutierrez J, Chan R, Batth T S, et al. 2013. Metabolic engineering of *Escherichia coli* for limonene and perillyl alcohol production. Metabolic Engineering 19:33-41.
4. Ambati R R, Moi P S, Ravi S, and Aswthanarayana R G. 2014. Astaxanthin: Sources, extraction, stability, biological activities and its commercial application—a review. Marine Drugs. 12(1):128-152.
5. Bar E, Rise M, Vishkautsan M, and Arad S. 1995. Pigment and structural changes in *Chlorella zofingiensis* upon light and nitrogen stress. Journal of Plant Physiology 146:527-534.

6. Ben-Amotz A, Gressel J, and Avron M. 1987. Massive accumulation of phytoene induced by norfluorazon in *Dunaliella bardawil* (Chlorophyceae) prevents recovery from photoinhibiton. Journal of Phycology 23(1):176-181.

7. Barbosa M J, Morais R and Choubert G. 1999. Effect of carotenoid source and dietary lipid content on blood astaxanthin concentration in rainbow trout (*Oncorhynchus mykiss*) Aquaculture 176(3-4):331-341.

8. Boyle N R and Morgan J A. 2009. Flux balance analysis of primary metabolism in *Chlamydomonas reinhardtii*. BMC Systems Biology 3:4.

9. Bumbak F, Cook S, Zachleder V, et al. 2011. Best practices in heterotrophic high cell density microalgal processes: achievements, potential, and possible limitations. Applied Microbiology Biotechnology 91:31-46.

10. Cerutti H, Ma X, Msanne J, Repas T. 2011. RNA-mediated silencing in algae: Biological roles and tools for analysis of gene function. Eukaryot Cell. September 10(9): 1164-1172. doi: 10.1128/EC.05106-11.

11. Chen T, Liu H, Lii P, Xue L. 2009. Construction of *Dunaliella salina* heterotrophic expression vectors and identification of heterotrophically transformed algal strains. Sheng Wu Gong Cheng Xue Bao. 25(3):392-8 (Abstract only).

12. Chen T, Wei D, Chen G, et al. 2009. Employment of organic acids to enhance astaxanthin formation in heterotrophic *Chlorella zofingiensis*. Journal of Food Processing and Preservation 33:271-284.

13. Chekanov K, Lobakova E, Selyakh I, Semenova L, Sidorov R and Solovchenko A. 2014 Accumulation of Astaxanthin by a New *Haematococcus pluvialis* Strain BM1 from the White Sea Coastal Rocks (Russia). Marine Drugs 12, 4504-4520.

14. Chisti Y. 1999. Fermentation (Industrial): Basic Considerations. In: Robinson R, Batt C, and Patel P, eds. Encyclopedia of Food Microbiology. Academic Press, London, pp 663-674.

15. Chua, P R, Franklin S, Wee J, Desai R. 2011. Production of Soladiesel® from cellulosic feedstocks. *Energy Research and Development Division Final Project Report*, California Energy Commission.

16. Doebbe A, Rupprecht J, Beckman J, et al. 2007. Functional integration of the HUP1 hexose symporter gene into the genome of *C. reinhardtii*: Impacts on biological $H_2$ production. Journal of Biotechnology 131:27-33.

17. Fábregas J, Otero A, Maseda A, and Dominguez A. 2001. Two-stage cultures for the production of astaxanthin from *Haematococcus pluvialis*. Journal of Biotechnology 89:65-71.

18. Gimpel J A, Henríquez V, Mayfield S P. 2015. In Metabolic Engineering of Eukaryotic Microalgae: Potential and Challenges Come with Great Diversity. Front Microbiol. 6: 1376. doi: 10.3389/fmicb.2015.01376

19. Göksan T, Ak I, Kiliç C. 2011. Growth Characteristics of the Alga *Haematococcus pluvialis* Flotow as Affected by Nitrogen Source, Vitamin, Light and Aeration. Turkish Journal of Fisheries and Aquatic Sciences. 11: 377-383

20. Hata N, Ogbonn, J C, Hasegawa Y, et al. 2001. Production of astaxanthin by *Haematococcus pluvialis* in sequential heterotrophic-photoautotrophic culture. Journal of Applied Phycology 7: 399-406.

21. Hatlen B, O. Oaland, L Tvenning, O Breck, J V Jakobsen, J Skaret. 2013. Growth performance, feed utilization and product quality in slaughter size Atlantic salmon (*Salmo salar* L.) fed a diet with porcine blood meal, poultry oil and salmon oil. Aquaculture Nutrition 19:573-584.

22. Kazamia E, Risely A S, Howe C J, and Smith A G. 2014. An engineered community approach for industrial cultivation of microalgae. Industrial Biotechnology 10 (3): 184-190.

23. Kim E, Y Park, Y Kim. 2015. A Transformed Bacterium Expressing Double-Stranded RNA Specific to Integrin (31 Enhances Bt Toxin Efficacy against a Polyphagous Insect Pest, *Spodoptera exigua*. PLoS ONE 10(7): e0132631. doi:10.1371/journal. pone.0132631.

24. Kobayashi M, Kakizono T, Yamaguchi K, Nishio N, and Nagai S. 1992. Growth and astaxanthin formation of *Haematococcus pluvialis* in heterotrophic and mixotrophic conditions. Journal of Fermentation Bioengineering 74: 17-20.

25. Kobayashi M, Kurimura Y, and Tsuji Y. 1997. Light-independent, astaxanthin production by the green microalga *Haematococcus pluvialis* under salt stress. Biotechnology Letters 19(6):507-509.

26. Kumar A, Wang S, Ou R, Samrakandi M, Beerntsen B T, Sayre R T. 2013. Development of an RNAi based microalgal larvicide to control mosquitoes. MalariaWorld Journal 4(6): 1-7.

27. Lauersen K J, H Berger, J M Mussgnug, O Kruse. 2013. Efficient recombination protein production and secretion from nuclear transgenes in *Chlamydomonas reinhardtii*. J Biotechnol 167(2): 101-110.

28. Lee Y K and Zhang D H. 1999. Production of astaxanthin by *Haematococcus*. Chemicals from Microalgae 41-56.

29. Lewis L A and McCourt R M. 2004. Green algae and the origin of land plants. American Journal of Botany 91(10): 1535-1556.

30. Liu X and Osawa T. 2007. Cis astaxanthin and especially 9-cis astaxanthin exhibits a higher antioxidant activity in vitro compared to the all-trans isomer. Biochemical and biophysical research communications 357(1):187-193.

31. Lorenz R, Cysewski G. 2000. Commercial potential for *Haematococcus* microalgae as a natural source of astaxanthin. Trends in Biotechnology 18(4):160-167.

32. Lorenz R T. 1999. A technical review of *Haematococcus* algae. NatuRose™ Technical Bulletin #060, pp. 1-12. Cyanotech Corporation, Kailua-Kona, Hi.

33. Machado V, Rodriguez-Garcia M J. 2014. RNA Interference: A new Strategy in the Evolutionary Arms Race Between Human Control Strategies and Insect Pests. Folia Biologica (Krakow), vol. 62 No 4 doi:10.3409/fb62_4.335.

34. McCarthy S S, MC Kobayashi, KK Niyogi. 2004. White mutants of *Chlamydomonas reinhardtii* are defective in phytoene synthase. Genetics. 2004 November; 168(3): 1249-1257. doi: 10.1534/genetics.104.030635.

35. McVittie A. 1974. Flagellum mutants of *Chlamydomonas reinhardii*. J General Microbiology 71:525-540.

36. Morales-Sanchez D, OA Martinez-Rodriguez, J Kyndt, and A Martinez. 2015. Heterotrophic growth of microalgae: metabolic aspects. World J Microbiol Biotechnol 31:1-9.

37. Muhaemin M and DRF Kaswadji. 2010. Biomass nutrient profiles of marine microalgae *Dunaliella salina*. J Penelitian Sains 13: 13313-64-13313-67.

38. Orosa M, Tones E, Fidalgo P, and Abalde J. 2000. Production and analysis of secondary carotenoids in green algae. Journal of Applied Phycology 12:553-556.

39. Rise M, Cohen E, Vishkautsan M, et al. 1994. Accumulation of secondary carotenoids in *Chlorella zofingiensis*. Journal of Plant Physiology 144:287-292.
40. Sambrook J F and DW Russell. 2001 Molecular Cloning: A Laboratory Manual, 3rd edition, Cold Spring Harbor Press, 2100 pp.
41. Scaife M A, Nguyen GTDT, Rico J, et al. 2015. Establishing *Chlamydomonas reinhardtii* as an industrial biotechnology host. The Plant Journal 82:532-546.
42. Schmidt I, Schewe H, Gassel S, et al. 2011. Biotechnological production of astaxanthin with *Phaffia rhodozyma/Xanthophyllomyces dendrorhous*. Applied Microbiology and Biotechnology 89:555-571.
43. Scranton M A, JT Olstrand, FJ Fields, SP Mayfield. 2015. *Chlamydomonas* as a model for biofuels and bioproducts production. Plant Journal 82: 523-531.
44. Sharon-Gojman R, Maimon E, Leu S, Zarka A, Boussiba S. 2015. Advanced methods for genetic engineering of *Haematococcus pluvialis* (Chlorophyceae, Volvocales). Algal Research, 10:8-15.
45. Solymosi K, N Latruffe, A Morant-Manceau, B. Schoefs. 2015. Food colour additives of natural origin. In: Colour additives for foods and beverages: Development, safety and applications (Scotter M J, ed). Woodhead Publishing Series in Food Science, Technology & Nutrition No. 279, Elsevier, pp 3-34.
46. Somchai P, Jitrakorn S, Thitamadee S, Meetam M, Saksmerprome V. 2016. Use of microalgae *Chlamydomonas reinhardtii* for production of double-stranded RNA against shrimp virus. Aquaculture Reports 3: 178-183.
47. Spijkerman E, Wacker A, Weithoff G, Leya T. 2012. Elemental and fatty acid composition of snow algae in Arctic habitats. Frontiers in Microbiology 3: 380.
48. Stemmer W P, Crameri A, Ha K D, Brennan T M, Heyneker H L. 1995. Single-step assembly of a gene and entire plasmid from large numbers of oligodeoxyrobnucleotides. Gene 64(1):49-53.
49. Syrenne R D and Yuan J S. 2014. Production of Limonene, a Volatile Monoterpene, in the Freshwater Algae *Chlamydomonas reinhardtii*. http://www.energy.gov/sites/prod/files/2014/07/f18/naabb_full_final_report_section_III.pdf, pp 27-28.
50. Tjahjono A E, Hayama Y, Kakizono T, et al. 1994. Hyper-accumulation of astaxanthin in a green alga *Haematococcus pluvialis* at elevated temperatures. Biotechnology Letters 16, 133-138.
51. Tran D, Louime C, Võ T, Giordano M, et al. 2013. Identification of *Dunaliella viridis* using its markers. International Journal of Applied Science and Technology 3 (4): 118-126.
52. Ukibe K, Katsuragi T, Tani Y, and Takagi H. 2008. Efficient screening for astaxanthin-overproducing mutants of the yeast *Xanthophyllomyces dendrorhous* by flow cytometry. FEMS Microbiology Letters 286: 241-248.
53. Wang Y and Peng J. 2008. Growth-associated biosynthesis of astaxanthin in heterotrophic *Chlorella zofingiensis* (Chlorophyta). World Journal of Microbiology and Biotechnology 24 (9): 1915-1922.
54. Wang X, Ort D R, Yuan J S. 2015. Photosynthetic terpene hydrocarbon production for fuels and chemicals. Plant Biotechnology Journal 13:137-146.
55. Wrolstad R E and CA Culver. 2012. Alternatives to those artificial FD&C food colorants. Annual Review of Food Science and Technology Vol. 3: 59-77.
56. Yu J and Takahashi P. 2007. Biophotolysis-based hydrogen production by cyanobacteria and green algae. Communicating Current Research and Educational Topics and Trends in Applied Microbiology. January 2007; 1.
57. Yuan J P, J Peng, K Yin, JH Wang. 2011. Potential health-promoting benefits of astaxanthin: A high value carotenoid mostly from microalgae. Mol Nutr Food Res 55: 150-165.
58. Zhang W, Chen F, Johns M R. 1999. Kinetic models for heterotrophic growth of *Chlamydomanas reinhardtii* in batch and fed-batch cultures. Process Biochemistry 35: 385-389.
59. Zhang J, SA Khan, C Hasse, S Ruf, DG Heckel, R Bock. 2015. Full crop protection from an insect pest by expression of long double-stranded RNAs in plastids. Science 347 (6225): 991-994 DOI:10.1126/science.1261680.

Patents and Patent Application Publications

1. U.S. Pat. No. 6,022,701
2. U.S. Pat. No. 5,882,849
3. U.S. Pat. No. 8,206,721
4. EP1724357 (US20080038774)
5. EP2878676 (US20150252391)
6. US20120264195
7. EP1995325
8. U.S. Pat. No. 8,404,468
9. U.S. Pat. No. 8,911,966
10. U.S. Pat. No. 8,278,090
11. U.S. Pat. No. 7,329,789
12. EP20030721175
13. US20090214475
14. US20090317878
15. US20120171733
16. U.S. Pat. No. 4,683,202
17. US20090317878
18. U.S. Pat. No. 7,135,620
19. U.S. Pat. No. 7,618,819
20. U.S. Pat. No. 7,129,392
21. WO2003027267
22. U.S. Pat. No. 9,487,790

What is claimed is:

1. A method for synthesizing a product of interest, the method comprising:
providing an organic acid as a salt-free carbon source in a culture medium and to maintain a pH of 8.5 or less;
providing a microalgal cell that produces the product of interest, wherein the microalgal cell is a facultative heterotroph and is classified as part of the order Chlamydomonadales;
providing dissolved oxygen at a concentration of at least 30%;
providing an aeration rate of at least 0.40 vessel volumes per minute;
providing components of the culture medium to the culture medium in a fed-batch manner;
culturing the microalgal cell in the culture medium in the dark to produce from the microalgal cell a microalgal culture comprising microalgal cells;
isolating the microalgal cells from the microalgal culture after the cells reach a density of at least 6 g/L but before the cells in the microalgal culture undergo cell differentiation into cysts, wherein the density of 6 g/L is achieved within 120 hours of the initiation of the microalgal cell culturing; and
purifying the product of interest from the isolated microalgal cells or obtaining a microalgal biomass comprising the microalgal cells as the product of interest.

2. The method of claim 1, wherein the microalgal cell is a facultative heterotroph that is rendered an obligate heterotroph.

3. The method of claim 1, wherein the product of interest is a microalgal biomass comprising the microalgal cells.

4. The method of claim 1, wherein the product of interest is a pigment, terpene, or recombinant molecule.

5. The method of claim 4, wherein the pigment is a carotenoid, or isoprenoid.

6. The method of claim 4, wherein the pigment is astaxanthin, lutein, lycopene, zeaxanthin, canthaxanthin, carotene, phytofluene, phytoene, or any combination thereof.

7. The method of claim 4, wherein the terpene is pinene, limonene, or geranylgeranyl pyrophosphate or any combination thereof.

8. The method of claim 4, wherein the recombinant molecule is a double stranded RNA (dsRNA) or heterologous protein.

9. The method of claim 5, wherein the cells of the microalgal culture before they undergo cell differentiation into cysts produce the pigment at a specific productivity rate of at least 0.33 mg/L-hour.

10. The method of claim 1, wherein the step of culturing is conducted for a period of less than one week.

11. The method of claim 1, wherein the heterotrophic growth and synthesis of the product of interest occurs during the step of culturing, and wherein the step of culturing is performed under a fed-batch fermentation of the organic acid source and a nutrient source that is not organic acid.

12. The method of claim 1, wherein the synthesis of the product of interest occurs in the culture medium depleted of nutrients of one or more of sulfate, phosphate, nitrate, and urea in the presence of replete carbon.

13. The method of claim 1, wherein the organic acid is acetic, citric, fumaric, glycolic, lactic, malic, proprionic, pyruvic, succinic, glucuronic, galacturonic, uronic, chlorogenic, or lignocellulosic acid.

14. The method of claim 1, wherein the culture medium comprises urea as a primary source of nitrogen.

15. The method of claim 1, wherein the method further comprises one or more steps of drying, grinding, lysing, and extracting the microalgal cell.

16. The method of claim 1, wherein the microalgal cell is a *Haematococcus* spp., *Chlamydomonas* spp., *Chloromonas* spp., *Dunaliella* spp., or *Chlamydocapsa* spp.

17. The method of claim 16, wherein the microalgal cell is replaced by a microbial cell type that preferentially metabolizes organic acid and urea.

18. The method of claim 1, wherein the microalgal cell is co-cultivated with a second cell that is a distinct species from the initial microalgal cells.

19. The method of claim 18, wherein the second cell uses a different carbon source to support its growth compared to the organic acid which supports the growth of the microalgal cell.

20. The method of claim 19, wherein the second cell consumes ammonium as a nitrogen source.

21. The method of claim 20, wherein the second cell type belongs to *Scenedesmus* spp., *Chlorella* spp., *Monoraphidium* spp., *Rhodotorula* spp., a diatom, a thraustochytrid, or a thraustochytrid-like microorganism.

22. The method of claim 18, wherein the microalgal cell belongs to a *Haematococcus* spp. and the second cell belongs to a *Chlamydomonas* spp.

23. The method of claim 1, wherein the synthesis of the product of interest occurs in the culture medium replete in one or more of sulfate, phosphate, nitrate, and urea.

24. The method of claim 12, wherein the synthesis of the product of interest occurs in the culture medium depleted of nutrients, wherein the culture medium is further combined with one or more extrinsic factors selected from an addition of osmoticum greater than 2.6 g/L, addition of 45 mM NaCl, addition of lactic acid in excess of 3 g/L, an increase in temperature 2 degrees Celsius above the growth temperature, and any combination thereof.

25. The method of claim 8, wherein the dsRNA is produced at a specific productivity rate of at least 0.04 mg/L-hour.

26. The method of claim 8, wherein the heterologous protein is produced at a specific productivity rate of at least 0.08 mg/L-hour.

27. The method of claim 1, wherein the microalgal culture has a specific growth rate of at least 0.6/day.

28. The method of claim 27, wherein the microalgal culture has a specific growth rate of at least 0.7/day.

29. The method of claim 27, wherein the microalgal culture has a specific growth rate of at least 1.0/day.

30. The method of claim 27, wherein the specific growth rate is maintained over a 96-hour period or longer.

31. The method of claim 28, wherein the specific growth rate is maintained over a 96-hour period or longer.

32. The method of claim 29, wherein the specific growth rate is maintained over a 96-hour period or longer.

33. The method of claim 9, wherein the specific productivity rate is at least 1.4 mg/L-hour.

34. The method of claim 9, wherein the specific productivity rate is at least 5.5 mg/L-hour.

35. The method of claim 10, wherein the step of culturing is conducted for a period of about 48 hours to about one week.

36. The method of claim 1, wherein the synthesis of the product of interest occurs when the culture medium has ammonium in excess of 2.5 mM, which accumulates from the cellular metabolism of urea in urea-replete medium.

37. The method of claim 36, wherein the synthesis of the product of interest occurs when the culture medium has ammonium in excess of 2.5 mM, wherein the culture medium is further combined with one or more extrinsic factors selected from an addition of osmoticum greater than 2.6 g/L, addition of 45 mM NaCl, addition of lactic acid in excess of 3 g/L, an increase in temperature 2 degrees Celsius above the growth temperature, and any combination thereof.

38. The method of claim 3 wherein the specific productivity rate is at least 50 mg/L-hr, at least 167 mg/L-hr, or at least 250 mg/L-hr.

39. The method of claim 1, wherein the carbon source is provided to the culture medium during culturing when the culture exceeds a pH set point of 8.5 or less.

40. The method of claim 3, wherein the microalgal biomass comprises pigmented microalgal vegetative cells of 40% or more dry weight protein.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer 585

<400> SEQUENCE: 1
```

```
ctgctatttc gacgacagtg                                                      20

<210> SEQ ID NO 2
<211> LENGTH: 20
<212> TYPE: DNA
<213> ORGANISM: Artificial Sequence
<220> FEATURE:
<223> OTHER INFORMATION: primer 586

<400> SEQUENCE: 2
acgagaactc cgctaaagtg                                                      20
```